United States Patent
Mukai et al.

(10) Patent No.: US 7,129,629 B2
(45) Date of Patent: Oct. 31, 2006

(54) METHOD OF EVALUATING WHITENESS, METHOD OF EVALUATING COMPARATIVE WHITENESS, LIGHT SOURCE AND LUMINAIRE

(75) Inventors: Kenji Mukai, Shijonawate (JP); Toshio Mori, Settsu (JP); Yoshio Manabe, Katano (JP); Yoshinori Ootaka, Takatsuki (JP); Masaaki Hama, Mukou (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/206,347

(22) Filed: Aug. 17, 2005

(65) Prior Publication Data
US 2006/0040138 A1   Feb. 23, 2006

Related U.S. Application Data

(62) Division of application No. 10/617,505, filed on Jul. 11, 2003, which is a division of application No. 09/880,612, filed on Jun. 13, 2001, now Pat. No. 6,947,130.

(30) Foreign Application Priority Data

Jun. 30, 2000  (JP) .............................. 2000-199523

(51) Int. Cl.
*H01J 61/44*  (2006.01)

(52) U.S. Cl. ...................... 313/487; 313/485; 313/486; 428/690; 252/301.4 R

(58) Field of Classification Search ..................... None
See application file for complete search history.

(56) References Cited

U.S. PATENT DOCUMENTS

| | | | |
|---|---|---|---|
| 4,469,798 A | 9/1984 | Nishino et al. | |
| 4,837,277 A | 6/1989 | Shigemoto | |
| 5,071,727 A | 12/1991 | Ikeda et al. | |
| 5,124,390 A | 6/1992 | Miller et al. | |
| 5,372,779 A | 12/1994 | Reti | |
| 5,714,836 A * | 2/1998 | Hunt et al. | 313/487 |
| 5,770,917 A | 6/1998 | Yano et al. | |
| 5,859,286 A | 1/1999 | Yamaguchi et al. | |
| 5,995,180 A | 11/1999 | Moriwaki et al. | |
| 6,020,959 A | 2/2000 | Imura | |
| 6,853,125 B1 * | 2/2005 | Irie et al. | 313/489 |

FOREIGN PATENT DOCUMENTS

| | | |
|---|---|---|
| EP | 0 595 527 A1 | 5/1994 |
| EP | 0 993 022 A1 | 4/2000 |
| JP | 61134636 | 6/1986 |
| JP | 9-120797 | 5/1997 |
| JP | 0 945 894 A1 | 9/1999 |

OTHER PUBLICATIONS

MacCormack et al., "New White Gold Alloys—Their Development on the Basis of Quantitative Colour Assessment," Gold Bull Jan. 1981, vol. 14, No. 1, pp. 19-24.

Ganz, E., "Whiteness Formulas: a Selection," Applied Optics, Apr. 1, 1979, USA, vol. 18, No. 7, pp. 1073-1078.

The CIE 1997 Interim Colour a Ppearance Model, CIE, Apr. 1998, Retrieved from the Internet www.colour.org/tc8-01, Abstract, pp. 1-21.

* cited by examiner

*Primary Examiner*—Marie Yamnitzky

(57) ABSTRACT

In evaluating whiteness of light from a light source or a luminaire, whiteness W is given by the following equation, $$W = -5.3C + 100,$$

wherein chroma C is determined by the CIE 1997 Interim Color Appearance Model (Simple Version).

26 Claims, 18 Drawing Sheets

FIG.11

|  | Phosphors | Weight percent |
|---|---|---|
| #1 | $BaMgAl_{10}O_{17}:Eu^{2+}$ | 19wt% |
|  | $Ce(Mg,Zn)Al_{11}O_{19}:Mn^{2+}$ | 29wt% |
|  | $LaPO_4:Ce^{3+},Tb^{3+}$ | 35wt% |
|  | $Y_2O_3:Eu^{3+}$ | 27wt% |
| #2 | $BaMgAl_{10}O_{17}:Eu^{2+},Mn^{2+}$ | 42wt% |
|  | $LaPO_4:Ce^{3+},Tb^{3+}$ | 15wt% |
|  | $Y_2O_3:Eu^{3+}$ | 43wt% |
| #3 | $(Ba,Ca,Sr,Mg)_{10}(PO_4)_6Cl_2:Eu^{2+}$ | 39wt% |
|  | $Ce(Mg,Zn)Al_{11}O_{19}:Mn^{2+}$ | 24wt% |
|  | $LaPO_4:Ce^{3+},Tb^{3+}$ | 4wt% |
|  | $Y_2O_3:Eu^{3+}$ | 33wt% |

METHOD OF EVALUATING WHITENESS, METHOD OF EVALUATING COMPARATIVE WHITENESS, LIGHT SOURCE AND LUMINAIRE

This is a divisional application of U.S. Ser. No. 10/617,505 filed on Jul. 11, 2003, which is a divisional application of U.S. Ser. No. 09/880,612, filed on Jun. 13, 2001 now U.S. Pat. No. 6,947,130.

BACKGROUND OF THE INVENTION (1) Field of the Invention

The present invention relates to a method of evaluating whiteness of light from a light source, a method of evaluating comparative whiteness, a light source and a luminaire that produce light with whiteness evaluated as being high by the method of evaluating whiteness.

(2) Related Art

Development of light sources and luminaries has conventionally been directed toward reproducing the original colors of an object to be illuminated faithfully. Specifically, luminaire that can provide color appearance of an object closer to that provided under a standard illuminant have achieved a high reputation. This can be objectively evaluated using the general color rendering index.

In recent years, however, desirable color appearance has been drawing attention instead of fidelity of color appearance. As a result, techniques for developing light sources and luminaries to render light colors as desired for specific applications are receiving attention. Some lamps have already been developed, such as those for making foods placed on the shelf look good or making plants at flower stores look more beautiful. To evaluate the desirable color appearance, visual clarity index is proposed in Japanese Laid-Open patent application No. 9-120797, which indicates how vivid an object color is rendered.

It is pointed out that light colors affect our perception of brightness (See Urabe et al., "Color Temperature of Light Source for Interior Lighting . . . The Effects on Brightness, (1) Impression from outside by Method of Paired Comparisons", Annual Conference of The Illuminating Engineering Institute of Japan, 1995.). In other words, the whiter a white object is rendered, the brighter the object appears to the human eyes. Also, as the feeling of whiteness increases, the Figure of an object looks neat. This would help make the visual environment more comfortable. Accordingly, it is desirable to use a luminaire with high whiteness while maintaining the vividity of color appearance.

However, evaluation measurements of such whiteness have conventionally relied on subjective judgments. For the same reasons, users have found it difficult to choose lighting devices.

SUMMARY OF THE INVENTION

The first object of the present invention is to provide a method of evaluating whiteness objectively.

The second object of the present invention is to provide a light source and a luminaire that realize lighting environments with high whiteness and vivid color appearance.

The first object can be achieved by a method of evaluating whiteness of light emitted from a light source, comprising the steps of: calculating chroma C, using a method defined by the CIE 1997 Interim Color Appearance Model (Simple Version); and calculating whiteness W from the chroma C using an equation (1), $$W = aC + b \quad (1)$$

where the coefficient a is a negative real number and the coefficient b is a positive real number. The second object can be achieved by a light source, being characterized by: emitting light whose whiteness is no smaller than 85 and whose visual clarity index is no smaller than 110, the whiteness W being calculated using chroma C of the light and an equation (3), $$W = -5.3C + 100 \quad (3)$$

wherein the chroma C is calculated using a method defined by the CIE 1997 Interim Color Appearance Model (Simple Version).

According to the present invention, the whiteness of light from a source can be evaluated objectively. Also, lighting environments with high whiteness and vivid color appearance can be provided.

BRIEF DESCRIPTION OF THE DRAWINGS

These and other objects, advantages and features of the invention will become apparent from the following description thereof taken in conjunction with the accompanying drawings that illustrate specific embodiments of the invention.

In the drawings:

FIG. 11 is a table showing phosphor combination examples, #1 to #3;

DESCRIPTION OF THE PREFERRED EMBODIMENTS

The following is a description of the preferred embodiments of the present invention, with reference to the drawings.

1. First Embodiment

The following is a description of a method of evaluating whiteness relating to a first embodiment of the present invention.

Figure 1:
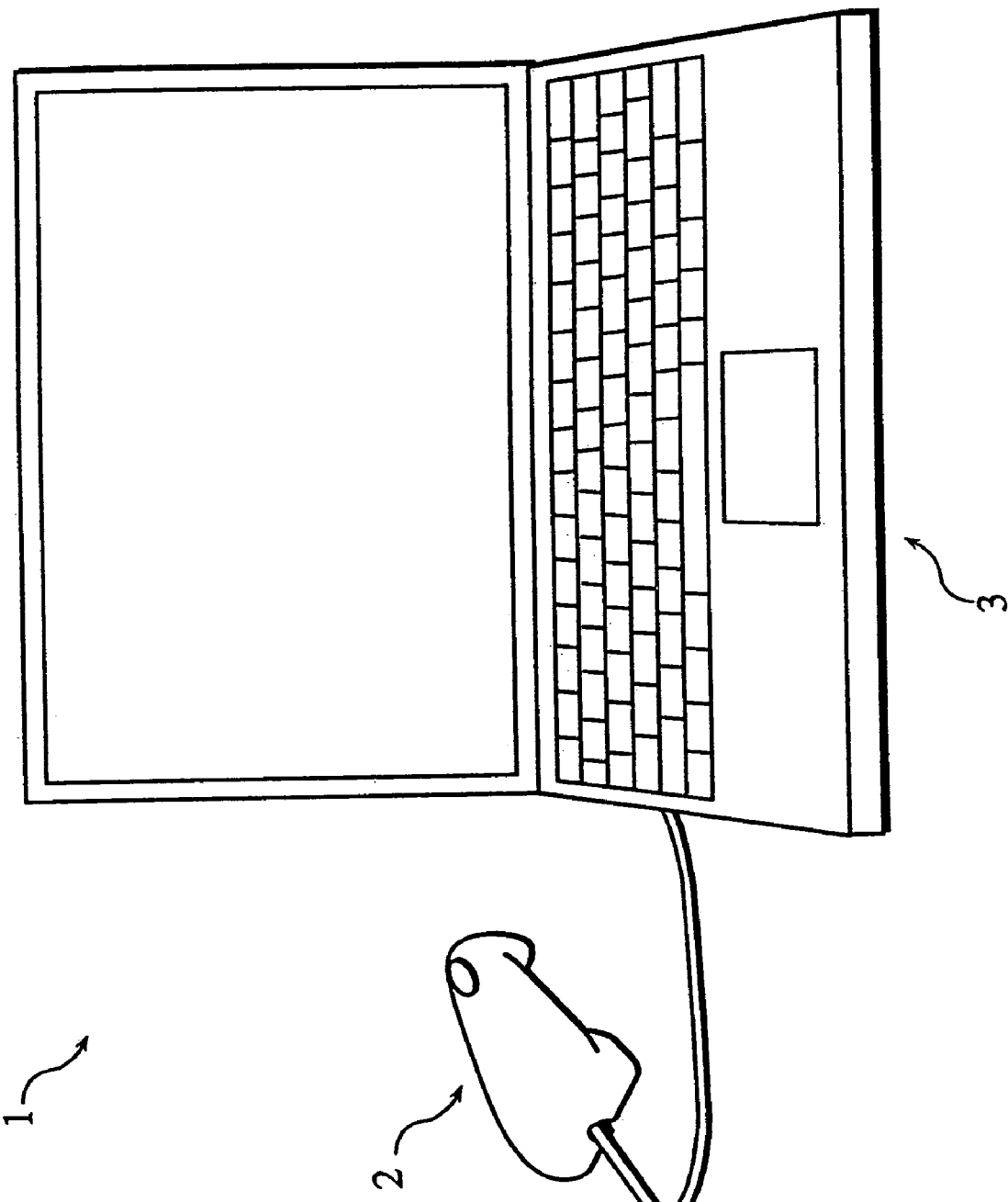
FIG. 1 shows a construction of a whiteness evaluating apparatus according to the first embodiment of the present invention.

FIG. 1 shows an appearance of whiteness evaluation apparatus 1. As shown in the figure, the whiteness evaluation apparatus 1 is comprised of the spectrophotometer 2 and the personal computer (hereafter referred to as PC) 3 connected to the spectrophotometer 2. The spectrophotometer 2 measures spectrum of light from a light source. Receiving spectral data from the spectrophotometer 2, the PC 3 calculates chroma and whiteness from the data, and then displays the whiteness on the computer screen.

Figure 2:
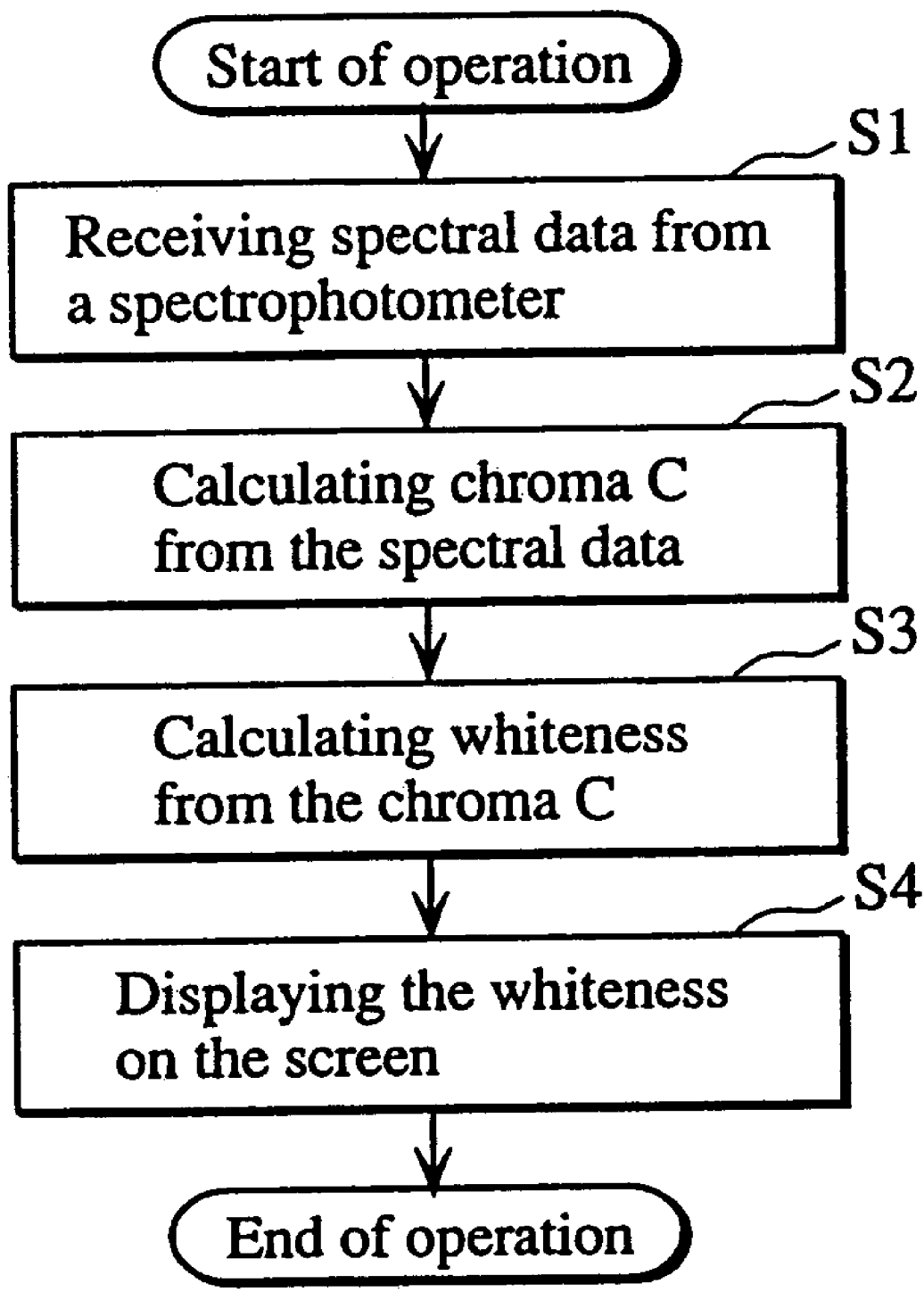
FIG. 2 is a flow chart describing the steps that the apparatus takes.

FIG. 2 is a flow chart illustrating the procedure the PC 3 follows to process spectral data passed by the spectrophotometer 2, until it completes the calculation of whiteness. First, the PC 3 receives spectral data from the spectrophotometer 2 (Step S1). Secondly, the PC 3 calculates chroma C in accordance with the definition of The CIE 1997 Interim Color Appearance Model (Simple Version) (hereafter referred to as CIE Model. CIE stands for Commission Internationale de Léclairage) (Step S2). Thirdly, it substitutes the chroma for C in the following equation (A) to produce whiteness W (Step S3).

$$W = -5.3C + 100 \quad (A)$$

Finally, the PC 3 displays whiteness W obtained from Step S3 on the screen (Step S4), and completes the processing.

It is understood that a light source that gives a feeling of higher whiteness has relatively lower chroma. In an experiment using the same light sources and color chips, it was found that a correlation exists between subjective evaluation of whiteness and chroma defined by the above CIE Model. The subjective evaluation is determined by subjects in an experiment, where they evaluate how white color chips appear under light sources on the scale from 0 to 100. When a subject feels that an object color is totally white, he or she scores 100, while an object color doesn't look white at all, it is given 0. In this way, the above subjective evaluation values were obtained.

Figure 3:
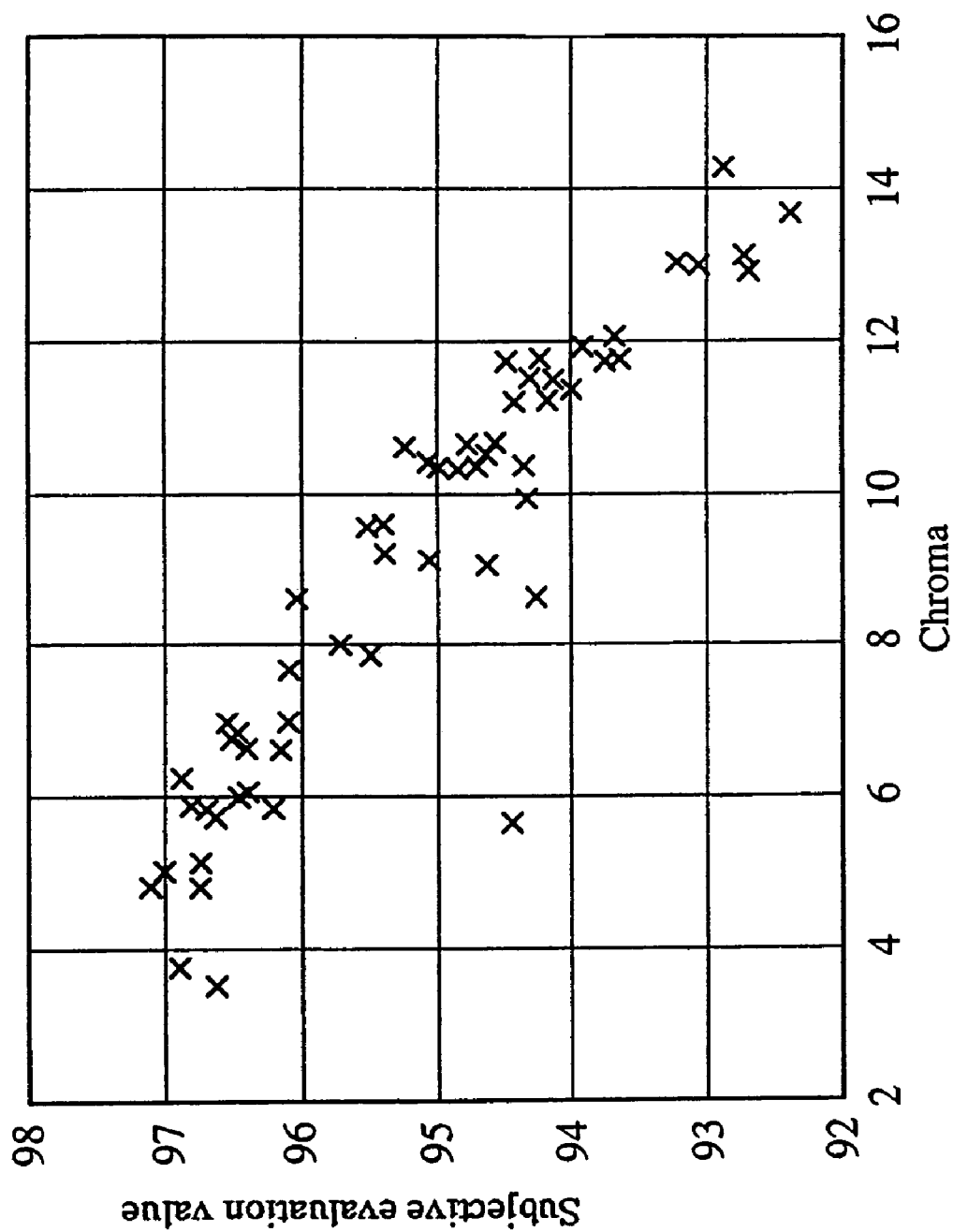
FIG. 3 is a graph showing a correlation of chroma with whiteness, where the chroma is determined by the CIE 1997 Interim Color Appearance Model (Simple Version), while whiteness is given in a subjective evaluation.

FIG. 3 is a scatter diagram to which the data obtained in the above experiment was plotted. The vertical axis represents subjective evaluation values and the horizontal axis represents chroma values. As shown in the diagram, the subjective evaluation values and the chroma have the relationship of a linear function that has a slope of a negative number. Here, the correlation coefficient between the chroma values and subjective evaluation values is 0.93. This demonstrates that subjective evaluation values are roughly proportional to chroma values. Therefore, by defining whiteness W using a linear expression of chroma C, as follows, $$W = aC + b$$

it is possible to evaluate whiteness objectively, without performing a subjective evaluation test.

The CIE Model was proposed by the CIE, so as to provide several indices with the highest accuracy among several other color appearance models. Using the model, various indices can be derived such as chroma, hue and brightness. Although many other models are available for quantifying chroma, the CIE Model is preferable for evaluating whiteness.

In the above equation (A), the coefficients a and b are determined so that a standard illuminant A with an illuminance of 500 lux has a whiteness of 50 and a light source with a chroma of 0 has a whiteness of 100. By such determining the coefficients a and b, whiteness of almost all general-purpose light sources can be contained in the range of 0 to 100. This is quite useful for evaluating light sources. Since chroma C always takes 0 or a positive value, with the equation (A) it is possible to evaluate characteristics of light sources on a scale from 0 to 100. Also, in this embodiment, the spectrophotometer 2 receives light directly from a light source and measures its spectrum. This is analogous to the case where the human eyes view an ideal white object whose spectral reflectance is 1.0 for visible light regions of 380 nm to 780 nm in the CIE Model.

2. Second Embodiment

The following is a description of a method of evaluating whiteness relating to the second embodiment of the present invention. In this embodiment, color chip N9.5 (manufactured by the Japan Color Research Institute) is used as an object to evaluate whiteness W of light from a light source. The color chip N9.5 is an available object whose spectral reflectance is the closest to a spectral reflectance 1.0 of an ideal white object. The Munsell value and Munsell chroma of this color chip is 9.5 and 0, respectively. Since the Munsell chroma is 0, Munsell hue is defined for the color chip.

Figure 4:
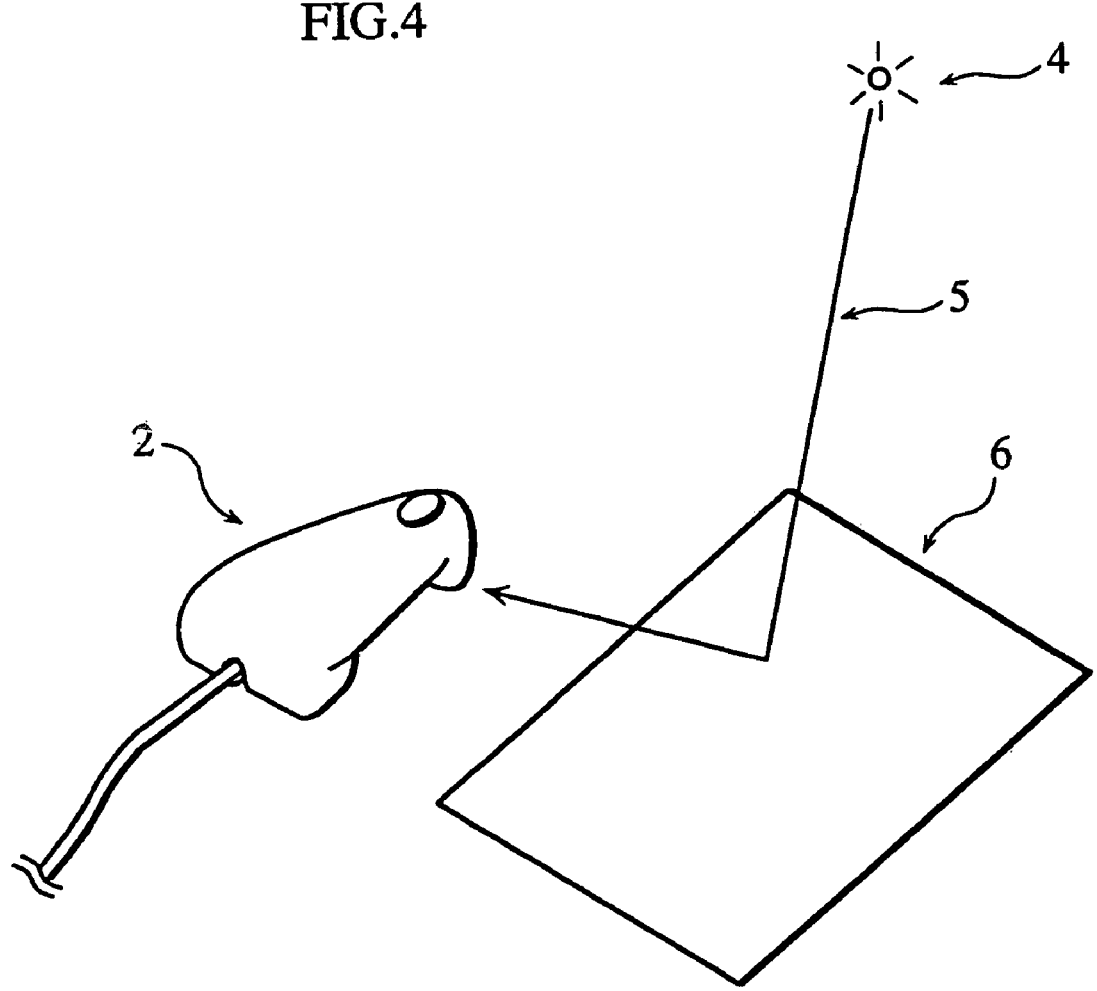
FIG. 4 shows an whiteness evaluating apparatus according to the second embodiment of the present invention.

FIG. 4 shows a construction of an apparatus for evaluating whiteness W of light 5 given off from a light source 4, using a color chip 6 as an object. Light 5 from a light source 4 is reflected on the surface of the color chip 6 before it is received by the spectrophotometer 2. The spectrophotometer 2 generates spectral data and sends it to a PC (not shown in the figure). The PC uses this spectral data to calculate chroma C. The PC then substitutes chroma C into the following equation, $$W = -4.4C + 100$$

to produce whiteness W for the light. The coefficients of the equation are determined so that a standard illuminant with an illuminance of 500 lux has a whiteness of 50 using of the color chip as an object, and that the light with a chroma of 0 has a whiteness of 100.

3. Third Embodiment

The following is a description of a method of evaluating whiteness relating to the third embodiment of the present invention. In this embodiment, a blank surface of a newspaper or a magazine, which is often viewed in daily life, is used as a visual object to evaluate whiteness of a light source. Such a blank surface has a Munsell value of about 8.0, a Munsell chroma of about 1.0 and a Munsell hue of about 5 GY, which are equivalent to those of color chip 5 GY 8.0/1.0 (manufactured by the Japan Color Research Institute). Accordingly, in this embodiment this color chip is used as an object to evaluate whiteness of light from a light source. The procedure used in this embodiment is roughly the same as that in the second embodiment, except that an equation used by a PC to calculate whiteness W from chroma C is $$W = -3.3C + 100$$

The two coefficients of this equation are determined so that a standard illuminant A with an illuminance of 500 lux has a whiteness of 50 using the color chip as an object, and that the standard illuminant A has with a chroma of 0 has a whiteness of 100.

Figure 5:
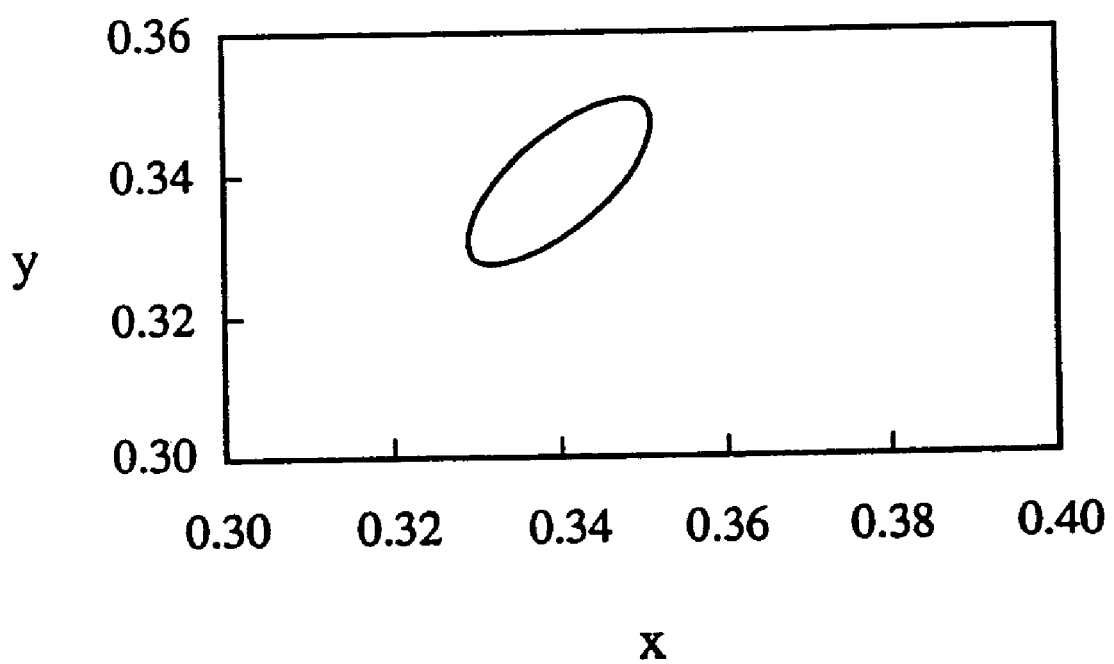
FIG. 5 shows a region on the CIE 1931 chromaticity diagram where the whiteness evaluation apparatus relating to the first embodiment assigns whiteness of 85 or greater.
Figure 6:
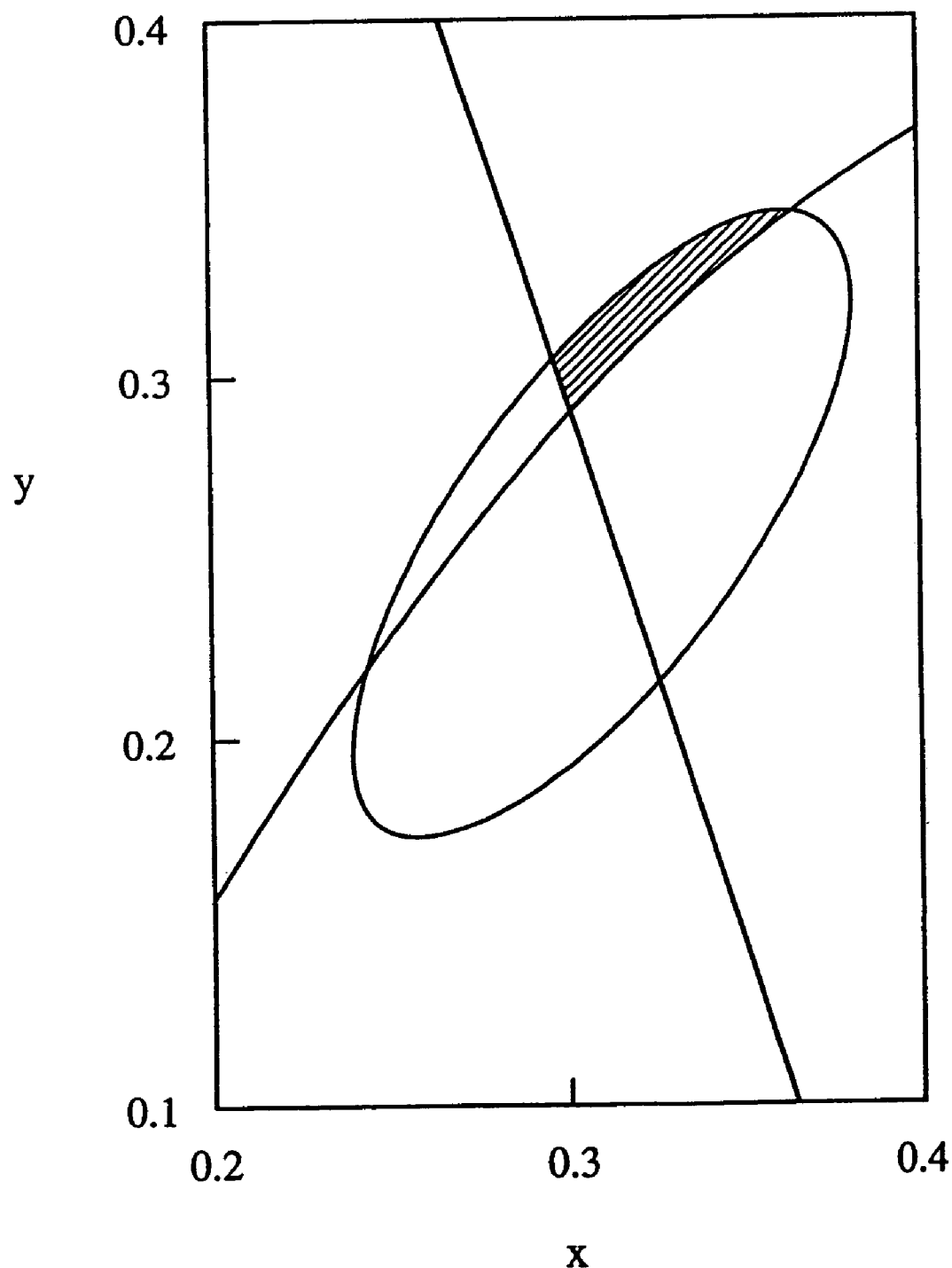
FIG. 6 shows a region on the CIE 1931 chromaticity diagram where a whiteness evaluation apparatus relating to the third embodiment assigns whiteness of 65 or greater.

The experiment showed that more than 50 percent of the subjects couldn't distinguish one light source from the other when a comparative whiteness between the two sources was no greater than 15 percent. Put another way, for more than 50 percent of the subjects, there is no difference between a light source with a whiteness of 85 and a light source with a whiteness of 100. The ellipse in FIG. 5 represents a region on the CIE 1931 chromaticity diagram, where whiteness of 85 or greater is shown using the apparatus of the first embodiment. This is the inside area of an ellipse which centers at chromaticity coordinates (x,y)=(0.3400, 0.3390), has the major axis and minor axis of 0.0150 long and 0.0060 long respectively, with the major axis inclining against the x-axis at an angle of 45°. Also, due to the characteristics of the objects used here, the minimum chroma value exceeds 0, and the maximum whiteness value is 75. Again, more than 50 percent of the subjects couldn't distinguish a source with a whiteness of 75 from the other light source when a comparative whiteness between the two sources was no greater than 15 percent. This means that a light source with a whiteness of 65 is evaluated to be the same as a light source with a whiteness of 75. As shown in FIG. 6, a region with a whiteness of 65 or greater as in the above case forms an ellipse on the CIE 1931 chromaticity diagram. The area is the inside of an ellipse which centers at chromaticity coordinates (x,y)=(0.3100, 0.2600), has the major axis and minor axis of 0.1050 long and 0.0400 long respectively, and with the major axis inclining against the x-axis at an angle of 52 degrees.

Light colors of light sources generally used for lighting are known to be within a range of $y \geq -2.63x^2 + 2.63x - 0.263$, $y \geq -3.09x + 1.22$, on the CIE 1931 chromaticity diagram. A diagonally shaded area in FIG. 6 represent a region which is evaluated to have a whiteness of 65 or greater by the whiteness evaluation apparatus of the third embodiment and which can be applied to general-purpose light sources. Due to the human visual characteristics, even with the same intensity of whiteness, while a light in bluish color can be used for commercial applications, a light in other colors including red and reddish colors can't serve for the purpose.

Regarding the visual clarity index proposed in Japanese Laid-Open Patent Application No.9-120797, it is reported that brightness of 1.1 times of a standard illuminant is perceived under a light source with a visual clarity index of 110, and when the index is 115, the brightness increases to 1.15 (See Hashimoto et al., "New Method of Specifying Color Rendering Properties of Light Sources based on the Feeling of Contrast", Journal of Illuminating Engineering Institute of Japan, pp. 639–671, Vol. 79, No. 11, 1995).

In sum, desirable light sources should have whiteness and visual clarity index of values as follows. When evaluating a whiteness of a light source, a color of light from the source should preferably be located within an ellipse, which centers at the chromaticity coordinates (x,y)=(0.3400, 0.3390), has major axis and minor axis of 0.0150 long and 0.0060 long respectively, with the major axis inclining against the x-axis at an angle of 45 degrees. At the same time, it is preferable if its visual clarity index is at 110 or greater, and more preferably at 115 or greater. When using newspaper as an object, it is desirable if a light color of a light source is specified within an ellipse that centers at the chromaticity coordinates (x,y)=(0.3100, 0.2600), where the length of major axis and minor axis is 0.1050 and 0.0400 respectively, and the major axis is inclining against the x-axis at an angle of 52 degrees, and the light color is within a range of $y \geq -2.63x^2 + 2.63X - 0.263$, $y \geq -3.09x + 1.22$. Its visual clarity index should preferably be at 110 or greater, and more preferably, at 115 or greater.

Figure 7:
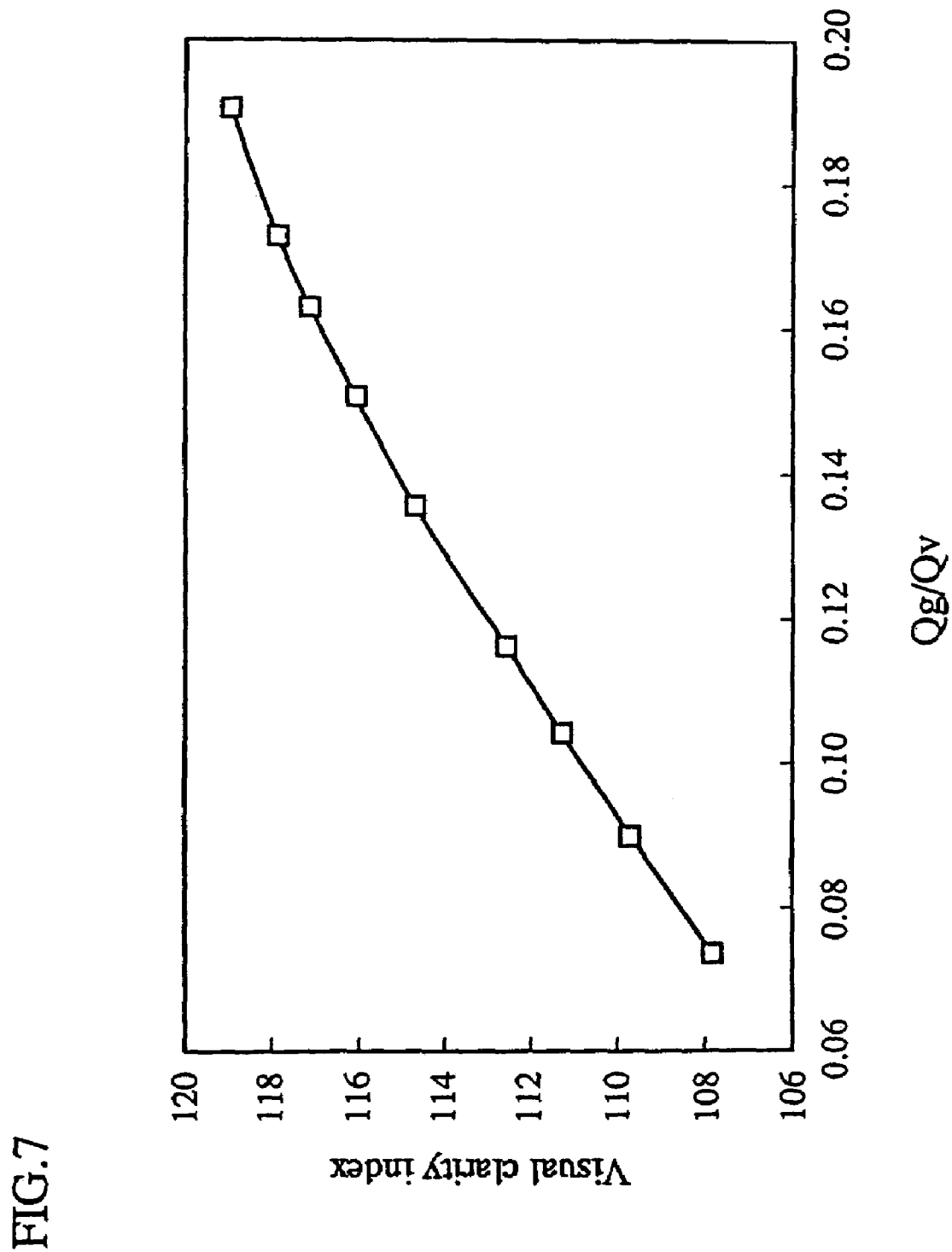
FIG. 7 is a graph showing the relation between the ratio Qg/Qv and the visual clarity index.

Under a three band fluorescent lamp, which is commonly used as a general-purpose light source, it was found that objects in several colors get more vivid and brighter, as radiant energy in a wavelength range from 505 nm to 530 nm increases against radiant energy in a wavelength from 380 nm to 780 nm. FIG. 7 is a graph showing the relationship between the visual clarity index and a ratio Qg/Qv under a fluorescent lamp with a correlated color temperature of 5200[K]. The ratio Qg/Qv refers to a ratio between radiant energy in a wavelength from 380 nm to 780 nm (visible band) (Qv) and radiant energy in a wavelength from 505 nm to 530 nm(Qg). As can be seen from FIG. 7, Qg/Qv varies in direct proportion to the visual clarity index. It was also found that the relationship between Qg/Qv and the visual clarity index varies according to the correlated color temperature.

Figure 8:
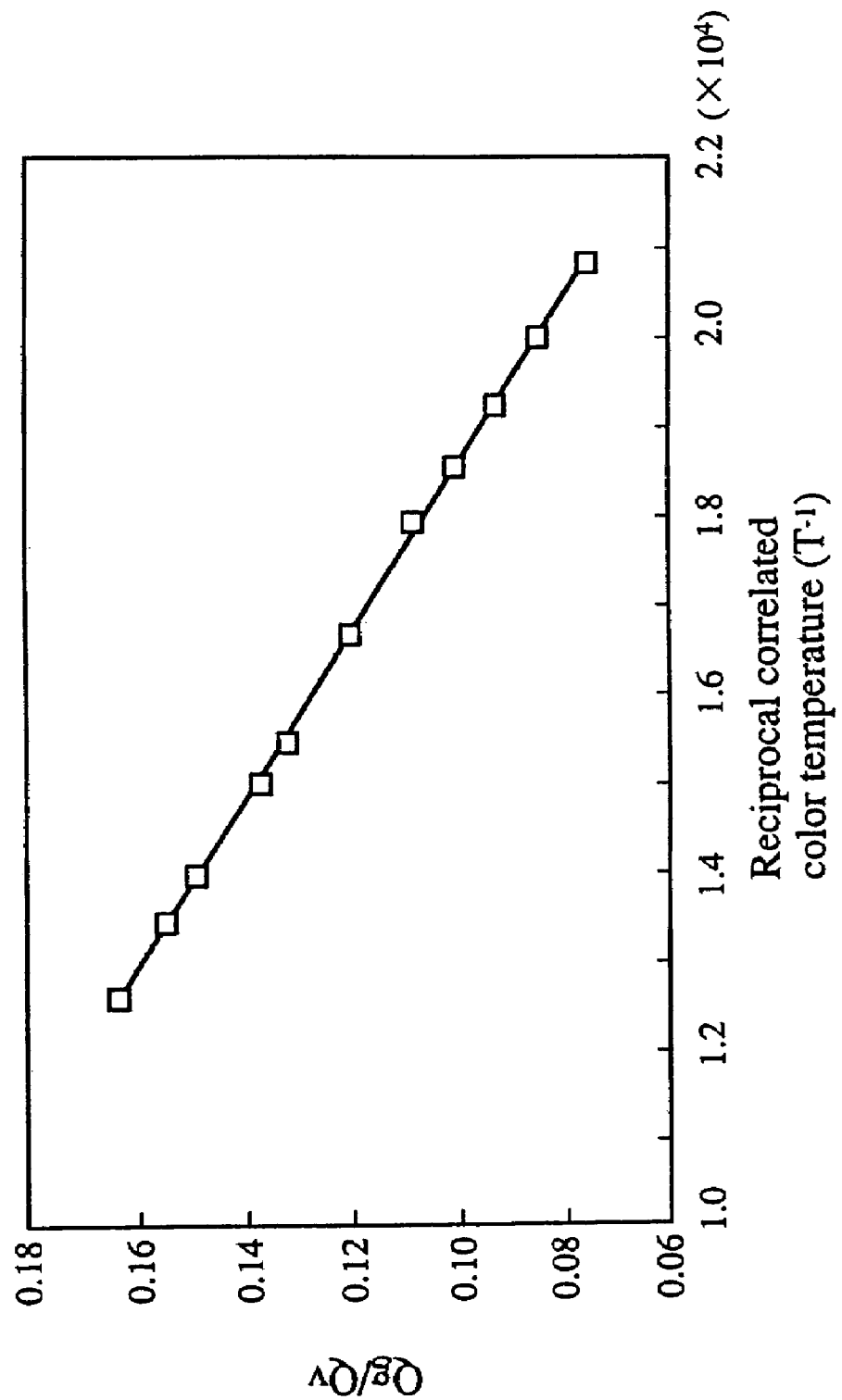
FIG. 8 is a graph showing the relation between the ratio Qg/Qv and reciprocal correlated color temperature ($T^{-1}$), for a fluorescent lamp whose visual clarity index is 110.
Figure 9:
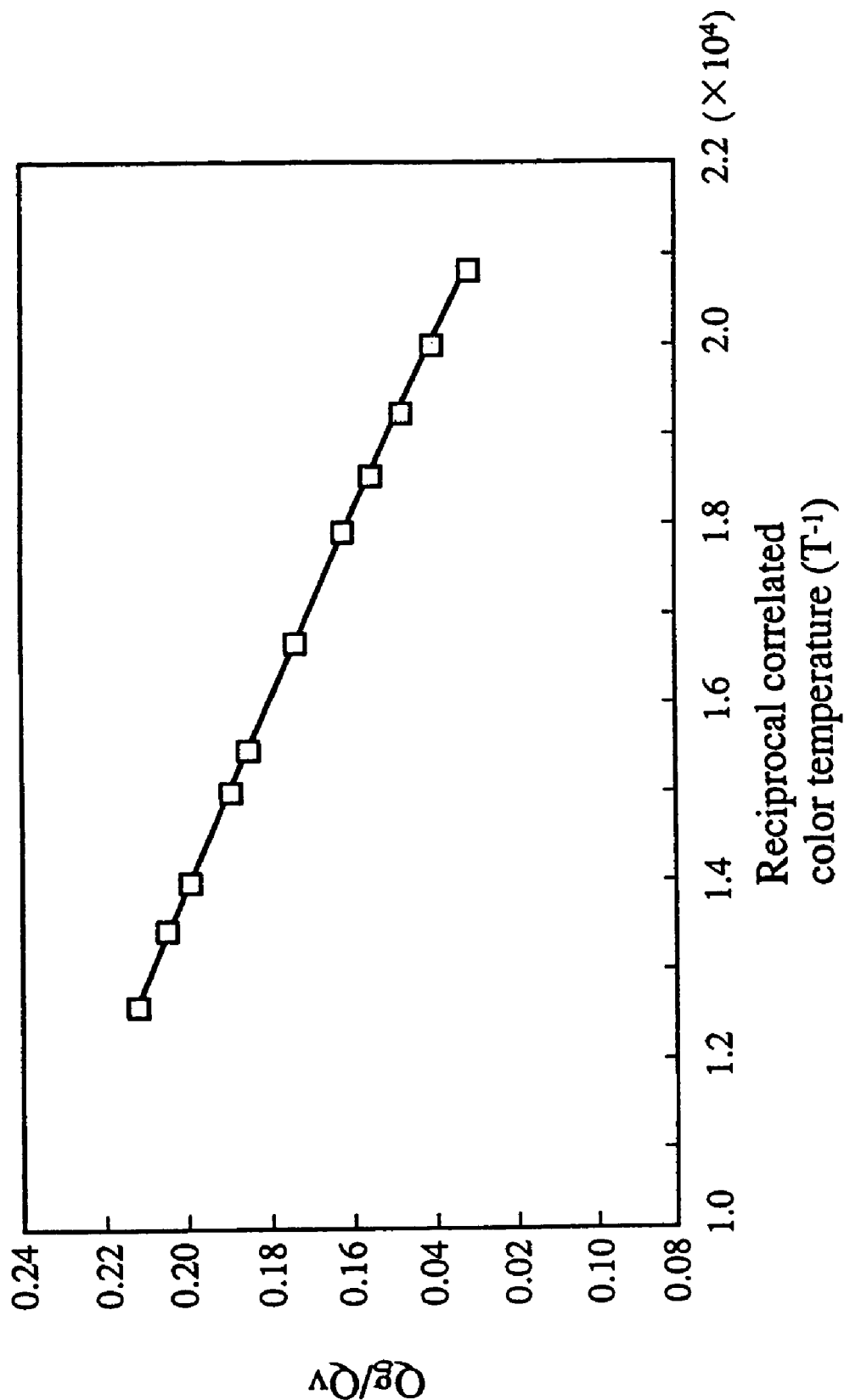
FIG. 9 is a graph showing the relation between the ratio Qg/Qv and the reciprocal correlated color temperature ($T^{-1}$), for a fluorescent lamp whose visual clarity index is 115.

FIG. 8 shows a graph showing the relationship between the ratio Qg/Qv and reciprocal correlated color temperature $T^{-1}[K^{-1}]$ under a fluorescent lamp with a visual clarity index of 110. As shown in FIG. 8, the reciprocal correlated color temperature $T^{-1}[K^{-1}]$ and Qg/Qv have a relationship of a linear function that has a slope of a negative number. As shown in FIG. 8, FIG. 9 shows a graph that describes the relationship between Qg/Qv and reciprocal correlated color temperature $T^{-1}[K^{-1}]$ under a fluorescent lamp with a visual clarity index of 115. Again, they have a relationship of a linear function that has a slope of a negative number.

In conclusion, when $Qg/Qv \geq -0.11 \times 10^4 \, T^{-1} + 0.30$, visual clarity index of a fluorescent lamp is 110 or greater, and when $Qg/Qv \geq -0.1 \times 10^4 \, T^{-4} + 0.33$, the index is 115 or greater. Therefore, by using the ratio Qg/Qv and the reciprocal correlated color temperature instead of visual color index, it will become easier to evaluate color appearance of an object.

It is also useful to be able to evaluate a whiteness of most of the general-purpose light sources in a score range of 0 to 100, when a whiteness under a standard illuminant A is 50 and a whiteness with a chroma of 0 is 100.

Forth Embodiment

The following is a description of how to achieve a light source of the characteristics, raising a fluorescent lamp as an example. Having high efficiency and color rendering properties, three band fluorescent lamps are used widely for lighting in houses, stores and offices. The three band fluorescent lamps contain rare earth phosphors that produce spectra in three wavelength ranges of 440 nm to 470 nm, 540 nm to 570 nm and 600 nm to 620 nm, where the strongest chromatic response is produced. Phosphors are blended together so that high energy is produced in a wavelength with high spectral luminous efficiency. To make a fluorescent lamp of the characteristics as mentioned above, another phosphor having spectrum at 505 nm to 530 nm should be added to the three phosphors.

Phosphor Composition

For a phosphor whose emission peak is located within a range from 440 nm to 470 nm, at least one of the phosphors containing bivalent europium as an emission center should be used. Phosphors in this group are selected from the group consisting of $BaMgAl_{10}O_{17}:Eu^{2+}$,
$BaMgAl_{10}O_{17}:Eu^{2+}, Mn^{2+}$ and
$(Ba,Ca,Sr,Mg)_{10}(PO_4)_6Cl_2:Eu^{2+}$.

In a phosphor containing $BaMgAl_{10}O_{17}$ as a host crystal such as $BaMgAl_{10}O_{17}:Eu^{2+}$ and
$BaMgAl_{10}O_{17}:Eu^{2+}, Mn^{2+}$ a portion of barium elements in the compounds could be replaced with another alkali earth metal element, such as calcium or strontium. By doing so, it is possible to shift the wavelength of peak emission of $Eu^{2+}$ or change the half-width of it.

For a phosphor whose emission peak is located within a range from 505 nm to 530 nm, at least one of the phosphors containing bivalent manganese as an emission center should be used. Phosphors in this group are selected from the group consisting of $BaMgAl_{10}O_{17}:Eu^{2+}, Mn^{2+}$,
$CeMgAl_{11}O_{19}:Mn^{2+}$,
$Ce(Mg, Zn)Al_{11}O_{19}:Mn^{2+}$,
$Zn_2SiO_4:Mn^{2+}$, and
$CeMgAl_{11}O_{19}:Tb^{3+}, Mn^{2+}$.

For a phosphor whose emission peak is located within a range from 540 nm to 570 nm, at least one of the phosphors containing trivalent terbium as an emission center should be used. Phosphors in this group are selected from the group consisting of $LaPO_4:Ce^{3+}, Tb^{3+}$ and
$CeMgAl_{11}O_{19}:Tb^{3+}$.

For a phosphor whose emission peak is located within a range from 600 nm to 620 nm, at least one of the phosphors containing trivalent europium as an emission center should be used. Phosphors in this group are selected from the group consisting of $Y_2O_3:Eu^{3+}$ and
$Gd_2O_3:Eu^{3+}$.

By combining four or more phosphors whose emission peaks are located within either of the four bands, a phosphor layer is formed and a fluorescent lamp of the present invention is realized.

It is also appreciated to employ a phosphor that has emission peaks in two of the four wavelength ranges. Since the phosphor of this kind can generate radiation in two wavelength ranges at a time, fewer phosphors are needed to form a phosphor layer.

Phosphors that emit radiation in two wavelength ranges include rare earth ions such as bivalent europium and trivalent cerium, and phosphors having bivalent manganese. When a fluorescent lamp is turned on, ultraviolet light is generated, whose wavelength is 253.7 nm, and the rare earth ions absorb and convert the light into visible light or light near UV spectrum. Some of the light energy is transmitted to the bivalent manganese, which in turn releases the energy in the form of light having a peak emission at 505 nm to 530 nm. Since bivalent manganese doesn't absorb ultraviolet radiation much, spectra of the light can be adjusted by changing the ratio of the rare earth ions to the bivalent manganese.

Phosphors having peak emissions both at 440 nm to 470 nm and 505 nm to 530 nm include phosphors that have bivalent europium and bivalent manganese. For example, the spectrum to be produced from a phosphor containing $BaMgAl_{10}O_{17}:Eu^{2}, Mn^{2+}$ can be adjusted by changing the amount of the bivalent europium or the bivalent manganese. As a percentage of bivalent manganese increases against bivalent europium, the bivalent europium produces lesser light having a peak at 440 nm to 470 nm. On the other hand, the bivalent manganese produces more light whose peak emission is at 505 nm to 530 nm, until the radiation from the bivalent europium becomes invisible and only the bivalent manganese produce light having a peak emission at 505 nm to 530 nm.

Phosphors having a peak emission at both 505 nm to 530 nm and 540 nm to 570 nm are phosphors that contain trivalent terbium and bivalent manganese, including $CeMgAl_{11}O_{19}:Tb^{3+}, Mn^{2+}$. In the case of $CeMgAl_{11}O_{19}:Tb^{3+}, Mn^{2+}$, trivalent cerium absorbs ultraviolet radiation, and then it transmits energy to trivalent terbium and bivalent manganese, which in turn produce light having a peak emission at 540 nm to 570 nm and light having a peak emission at 505 nm to 530 nm, respectively. At the same time, trivalent cerium produces light having an emission peak at 300 nm to 400 nm, but it is almost impossible to perceive the light because of its lower luminous efficiency. Therefore, visible light is light mainly from trivalent terbium and bivalent manganese. Since the trivalent cerium transmits energy to both the trivalent terbium and the bivalent manganese, spectrum of the light to be produced is adjustable by changing the amount of trivalent terbium and bivalent manganese, as long as the same percentage of trivalent cerium is contained.

In this specification, a group of three or more kinds of phosphors having emission peak in the wavelength ranges mentioned above are referred to as constituting a main component, when they account for 70 to 100 weight percent of all the phosphors contained in a phosphor layer. In other words, it is possible to add another phosphor as long as it doesn't exceed 30 percent of the entire phosphor layer, by weight. To improve color rendition, for example, phosphors are added whose emission peak is at 620 nm to 670 nm or in any other regions in which the color rendering effect improves. It is appreciated to add such phosphors in order to improve color rendition.

Building a Fluorescent Lamp

Figure 10:
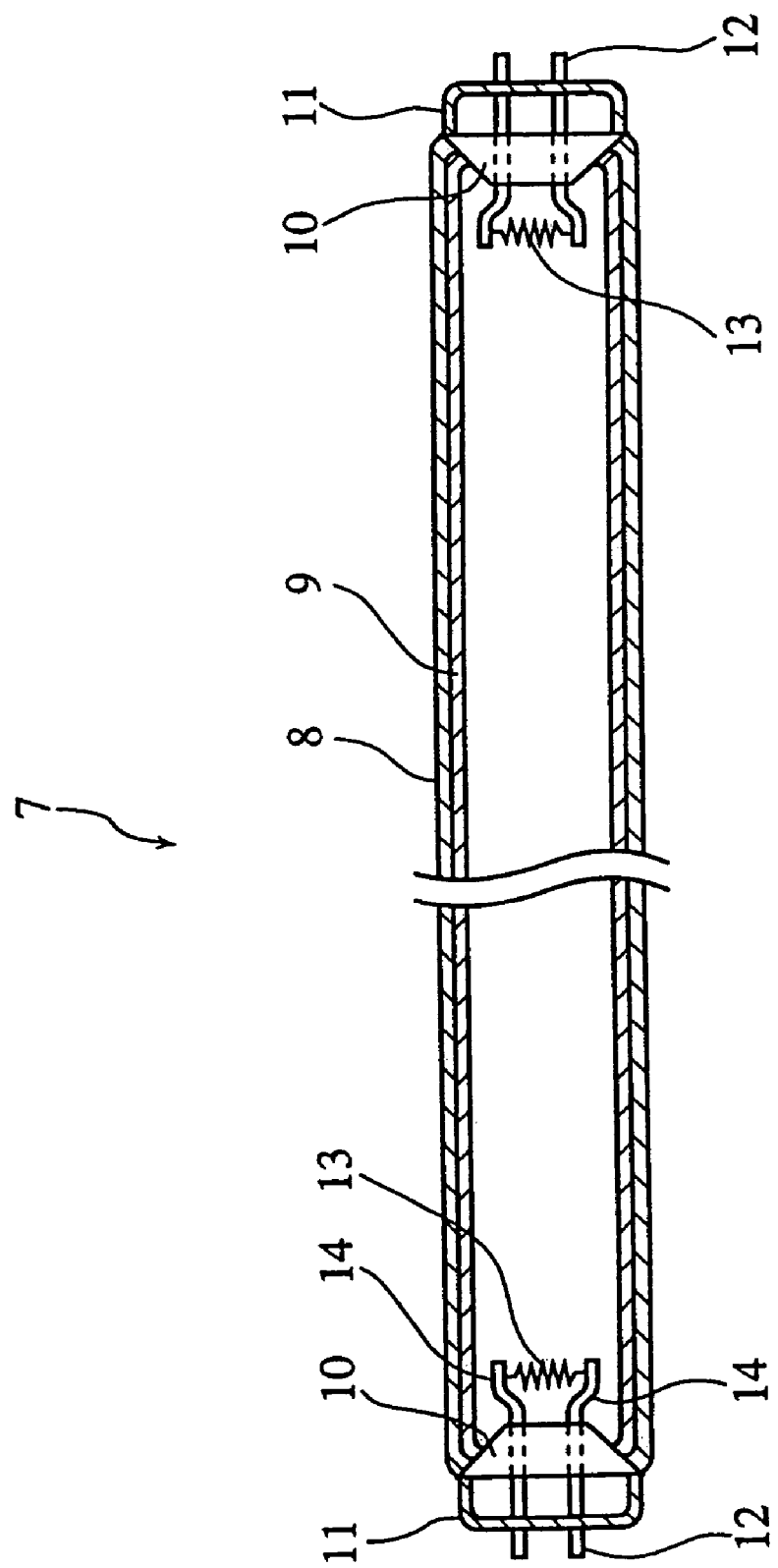
FIG. 10 shows a cross-section of a fluorescent lamp relating to the present invention.

The following is an explanation of how to build a fluorescent lamp using the above phosphors. We take a fluorescent lamp 7 in FIG. 10. FIG. 10 shows a longitudinal section of the fluorescent lamp 7. The fluorescent lamp 7 contains a phosphor layer 9 on the interior surface of a glass tube 8, which is sealed at both of the ends with stems 10. The stems 10 have lead wires 14 penetrating through them hermetically. The lead wires 14 are connected with filaments 13, and bonded to electrodes 12 which are supported by caps 11.

After blended in a specified proportion, the phosphors are adjusted and mixed with organic solvent, such as water and butyl acetate, and produce slurry. Aqueous polymers or polymers soluble in an organic solvent can be added to the mixture, so as to make the forming of films easier. A binding agent can also be added to strengthen bonds between phosphors and between a phosphor and a glass tube 8.

Then, the slurry is applied to the inside surface of the glass tube 8 and dried to form a phosphor layer 9. When it is confirmed that the phosphor layer 9 is formed, inert gases (such as argon gas) and mercury are flown into the glass tube 8, whose ends are then sealed with the stems 10. The caps 11 are bonded to the end of the glass tube 8, and the electrodes 12 and lead wires 14 are connected to the caps 11. In this way, the fluorescent lamp 7 relating to the present invention is achieved.

The method of building a slim-line fluorescent lamp is applicable to making circuline lamps and lamps in other shapes, on condition that the phosphors are added in a specified proportion.

FIG. 11 shows three types of fractional weight percent of the phosphor components #1 to #3. Phosphors in #1 consist of 19 percent of $BaMgAl_{10}O_{17}:Eu^{2+}$, 29 percent of $Ce(Mg,Zn)Al_{11}O_{19}:Mn^{2+}$, 35 percent of $LaPO_4:Ce^{3+}, Tb^{3+}$, and 27 percent of $Y_2O_3:Eu^{3+}$, by weight.

Phosphors in #2 consist of 42 percent of $BaMgAl_{10}O_{17}$, 15 percent of $LaPO_4:Ce^{3+},Tb^{3+}$, 43 percent of $Y_2O_3:Eu^{3+}$, by weight.

Phosphors in #3 consist of 39 percent of $(Ba,Ca,Sr,Mg)_{10}(PO_4)_6Cl_2:Eu^{2+}$, 24 percent of $Ce(Mg,Zn)Al_{11}O_{19}:Mn^{2+}$, 4 percent of $LaPO_4:Ce^{3+}, Tb^{3+}$, and 33 percent of $Y_2O_3:Eu^{3+}$, by weight.

Figure 12:
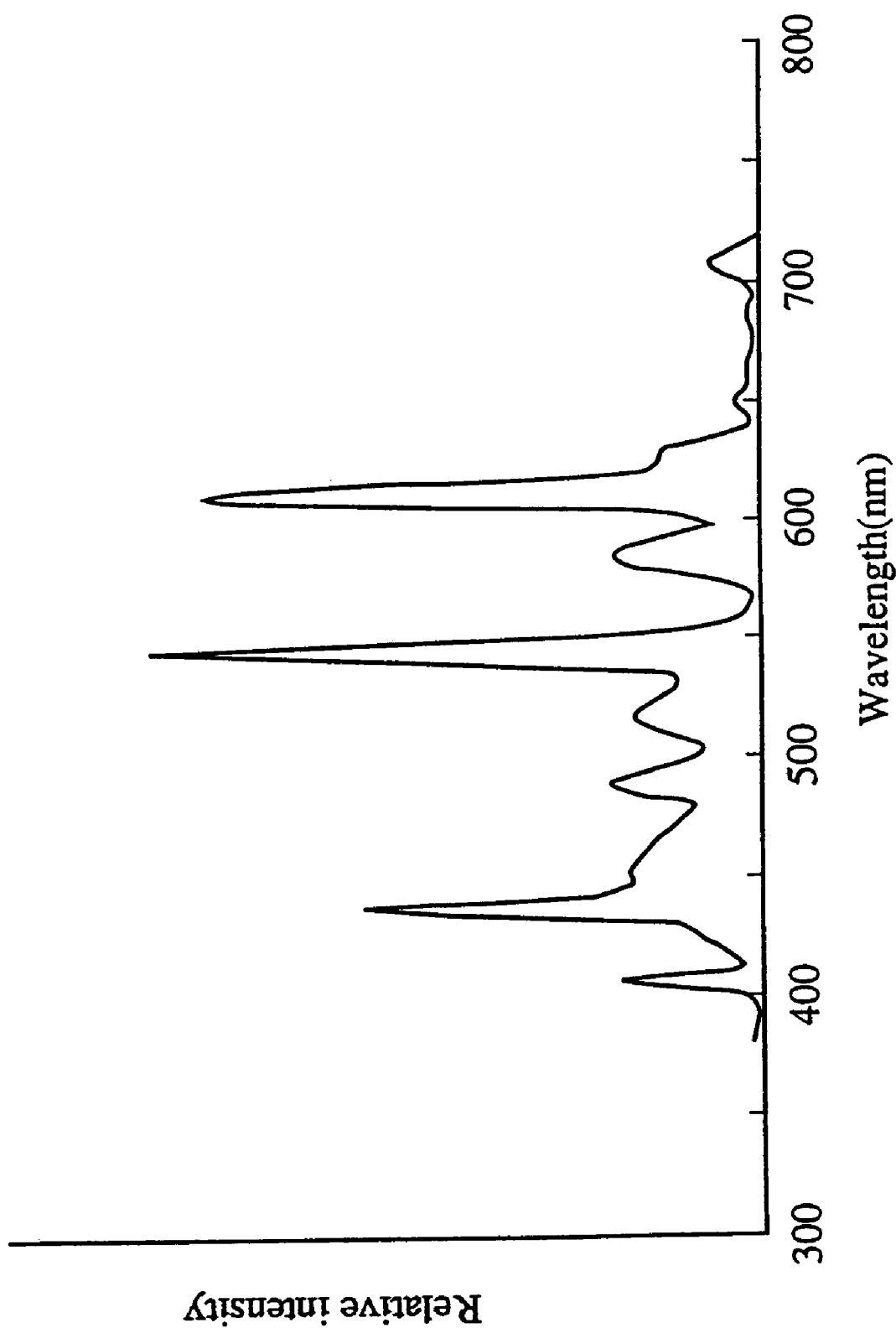
FIG. 12 shows a spectrum of light emitted from a 30 W circuline fluorescent lamp that uses the phosphor combination of #1.

FIG. 12 shows a spectrum of radiation emitted from a 30 W circuline fluorescent lamp (FCL30) that contains phosphors as shown in #1. By the whiteness evaluating apparatus used in the first embodiment, the lamp is evaluated to have a whiteness of 90.9, visual clarity index of 111 and chromaticity coordinates (x,y)=(0.3393, 0.3420). This means that the fluorescent lamp can provide an ideal light color. That its correlated color temperature is 5204[K] and Qg/Qv is 0.09 agrees with the visual clarity index mentioned above.

Figure 13:
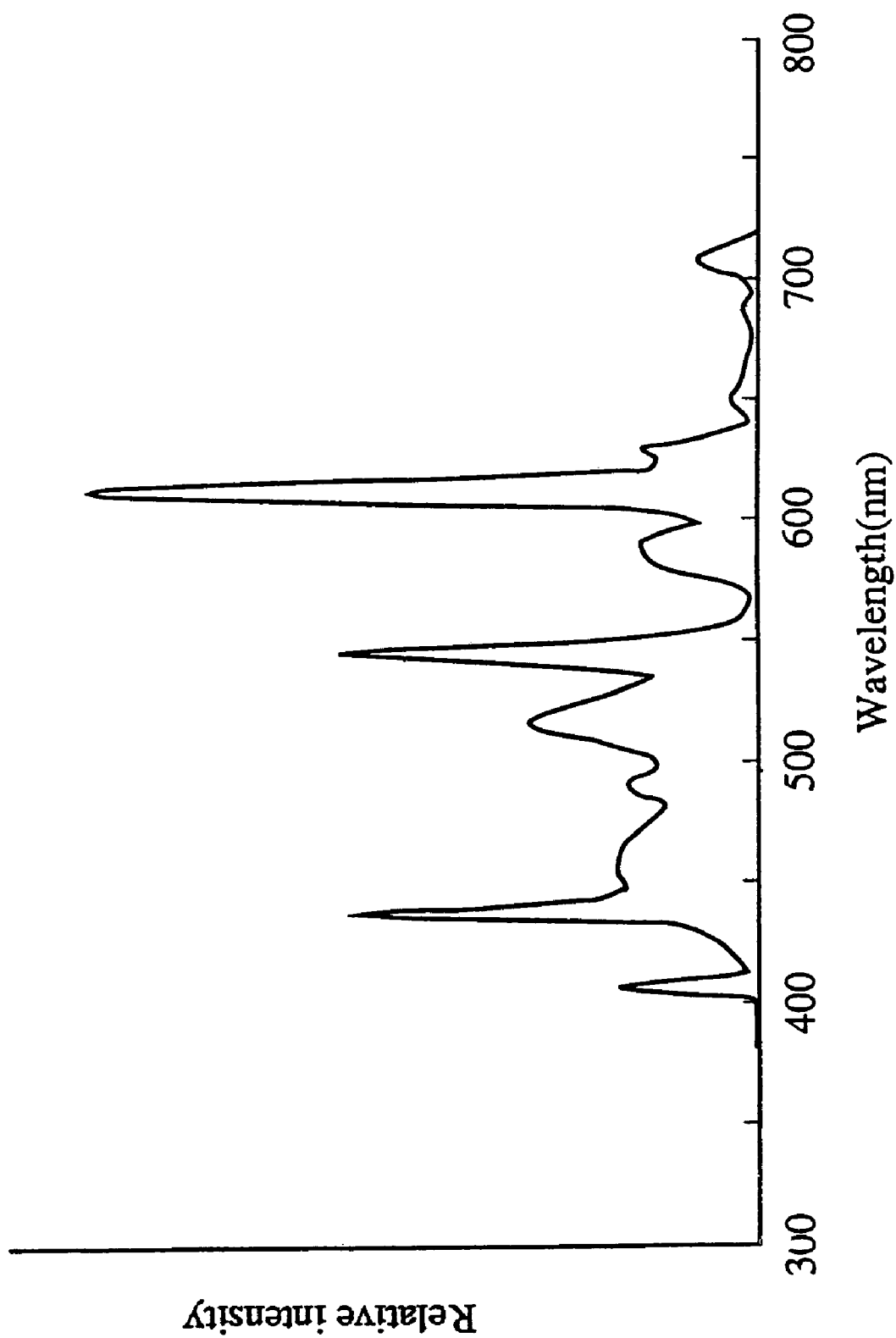
FIG. 13 shows the spectrum of light emitted from a 30 W circuline fluorescent lamp that uses the phosphor combination of #2.

FIG. 13 shows a spectrum of light emitted from a 30 W circuline fluorescent lamp (FCL30) that contains phosphors as shown in #2. By the whiteness evaluating apparatus used in the first embodiment, the lamp is evaluated to have a whiteness of 93.6, visual clarity index of 115 and chromaticity coordinates (x,y)=(0.3375, 0.3339) on the CIE 1931 chromaticity diagram. This means that the fluorescent lamp can provide an ideal light color. That the correlated color temperature is 5256[K] and Qg/Qv is 0.15 agrees with the visual clarity index mentioned above.

Figure 14:
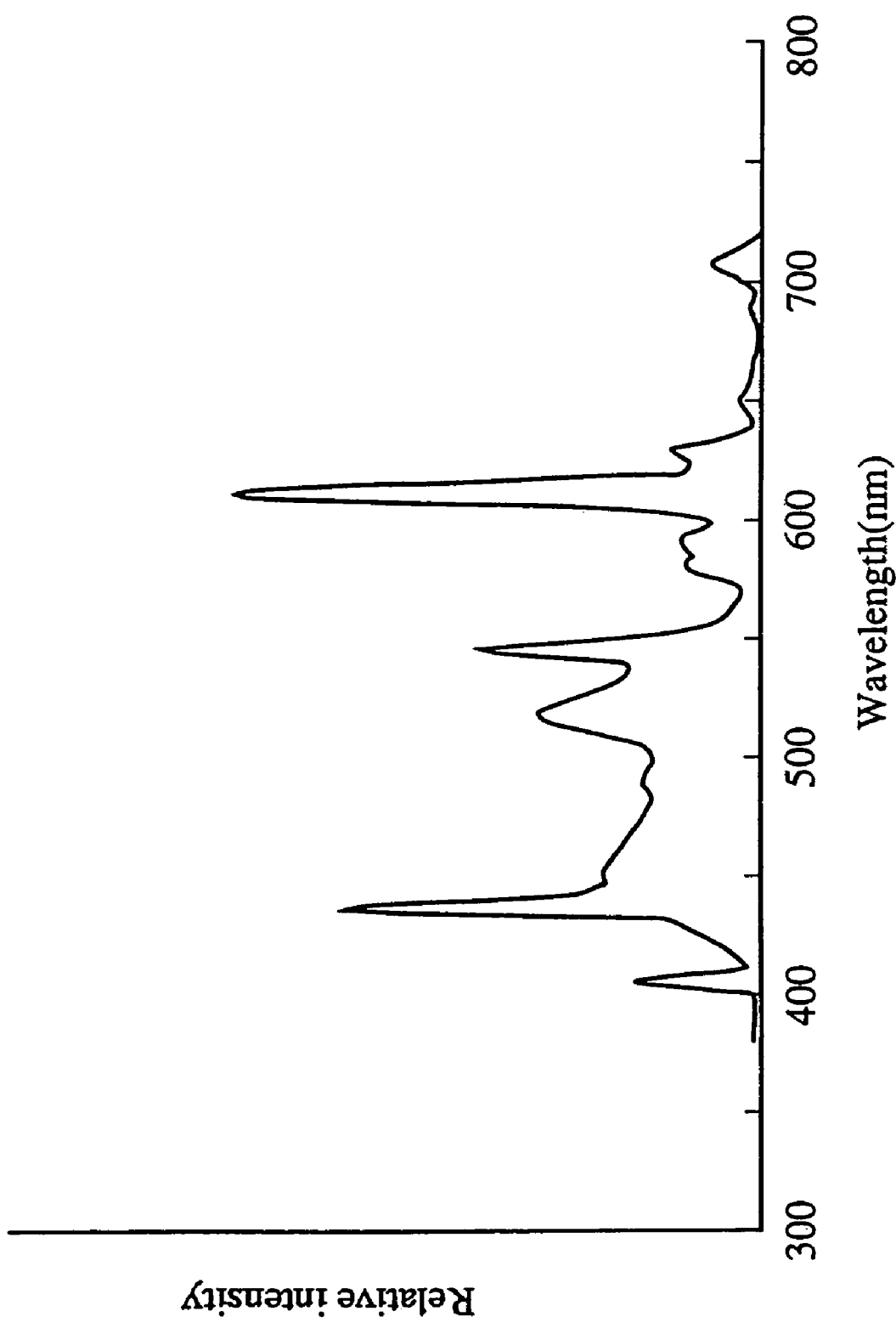
FIG. 14 shows the spectrum of light emitted from a 40 W slim-line fluorescent lamp that uses the phosphor combination of #3.

FIG. 14 shows a spectrum of radiation from a 40 W slim-line fluorescent lamp (FL40S) that contains phosphors as shown in #3. By the whiteness evaluating apparatus used in the third embodiment, the lamp is evaluated to have a whiteness of 68.6, visual clarity index of 110 and chromaticity coordinates (x,y)=(0.3057, 0.3084) on the CIE 1931 chromaticity diagram. This means that the fluorescent lamp can provide an ideal light color. That the correlated color temperature is 7170[K] and Qg/Qv is 0.17 agrees with the visual clarity index mentioned above. It is also confirmed from a subjective evaluation that under a fluorescent lamp containing phosphors as shown in #3, objects in various colors including newspapers and white objects look whiter and more vivid.

Figure 15:
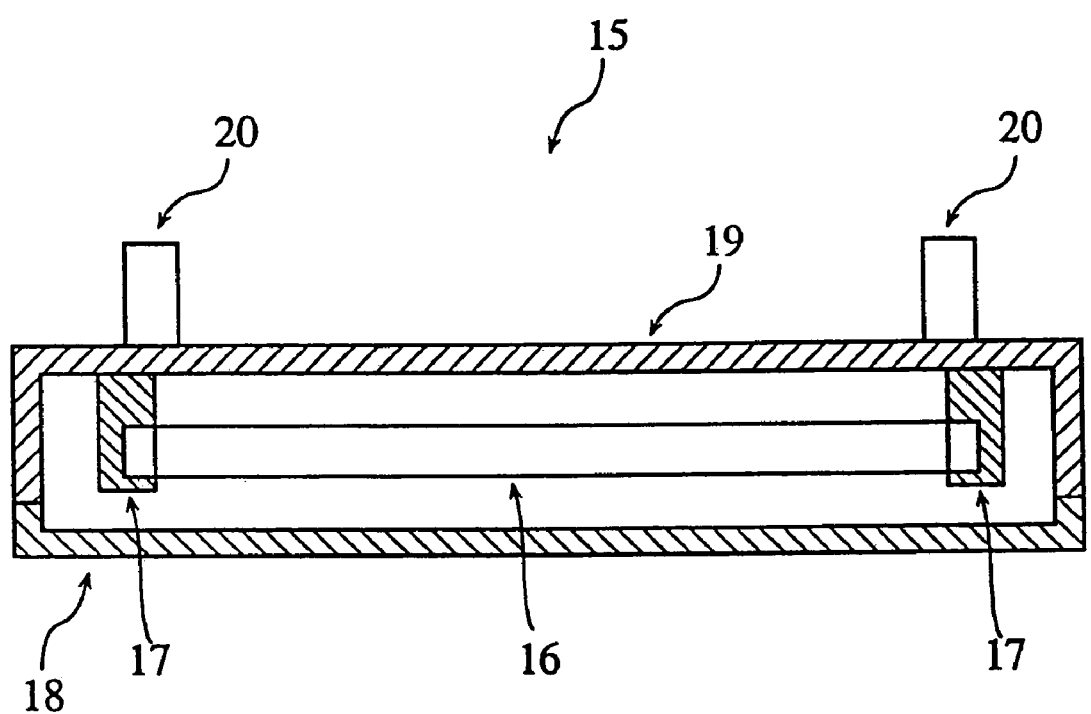
FIG. 15 shows a cross-section of a luminaire relating to the present invention.

FIG. 15 shows a longitudinal section of a luminaire 15 that contains the above fluorescent lamp. The luminaire 15 is comprised of a fluorescent lamp 16, first carriers 17 supporting the fluorescent lamp 16, a reflector 19 that reflects light from the fluorescent lamp 16, and a translucent cover 18 that allows light from the lamp 16 and reflected light from the reflector 19 to go through. The luminaire 15 is fixed on the ceiling or on the wall with second carriers 20. The reflector 19 is made from a material that doesn't absorb a particular radiation in visible bands, and therefore has a virtually uniform spectral reflectance in the visible bands. The translucent cover 18 is made from a material that doesn't absorb a particular radiation in visible bands, and therefore has a virtually uniform spectral transmittance in the visible bands. Using these components, a luminaire of the desired characteristics is achieved.

Even a luminaire lacking the translucent cover 18 can produce desirable light, with the reflector 19 made from the same materials as mentioned above. A luminaire having other forms of light sources than fluorescent lamps in it can also produce desirable light, so long as the light source have the characteristic requirements.

We have seen embodiments of the present invention by raising fluorescent lamps as a light source of excellent characteristics. But even a light source that fails to meet the requirement can produce desirable light, if it has several components. That is, if the light source has a reflector and a translucent cover, it is possible to convert light from a light source located inside the luminaire into light of the characteristics mentioned above and produce desired light.

Specifically speaking, the translucent cover should be made either from glass or plastic. A glass translucent cover is made by applying a dosage of metal ions that absorb light in particular wavelength ranges, such as $Cr^{3+}$, $Mn^{3+}$, $Fe^{3+}$, $Co^{2+}$, $Ni^{2+}$ and $Cu^{2+}$, to a glass and making a glass translucent cover in an intended form. The dosage of the metal ions should preferably be 15 mol weight percent or under of the entire glass. A plastic translucent cover is made by blending and kneading some inorganic and organic pigments into plastic materials before making a plastic translucent cover in an intended form. Those inorganic pigments include cobalt violet, cobalt blue, ultramarine, cobalt green, cobalt chrome green, titan yellow, red iron oxide and minium. As for the organic pigments, they are selected from a group consisting of dioxane compound, phthalocyanine compound, azo compound, perylene compound and pyrrolopyrrol compound. The pigment dosage should preferably be 5 weight percent or under of the entire plastic materials.

Spectral reflectance of a translucent cover can be adjusted by forming layers of plastic films that contain the light absorbing materials on the surface of it. Paints that contain the light absorbing materials coated on the surface of a glass or plastic translucent cover can also change the spectral reflectance. This also makes it possible to adjust spectral transmittance of a translucent cover easily. As for the spectral reflectance for a reflector, it can be adjusted by blending the light absorbing materials into a basic material that constitutes the reflector, or by forming layers containing the light absorbing materials on the surface of the basic material. The translucent cover and the reflector can be employed either in combination or separately, to provide the effect of the present invention.

We have explained the present invention in accordance with some of the embodiments, but they aren't the only forms of the application. It will be appreciated that the present invention is realized in other modifications, some of which are explained below.

Modifications (1) The following is an explanation of how to obtain chroma C for the embodiments, 1,2,3.

Figure 16:
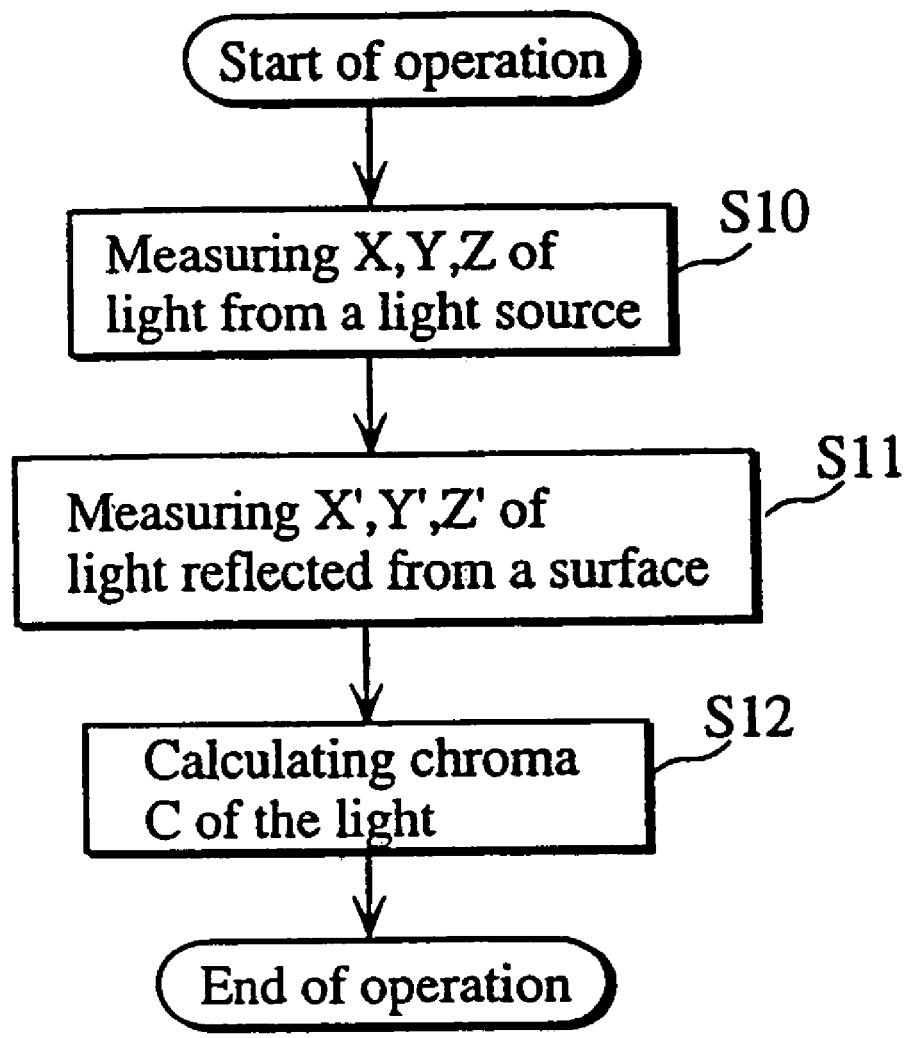
FIG. 16 is a flow chart showing the first procedure of calculating chroma according to a modification to the invention.

FIG. 16 shows a flow chart describing the processing contents to obtain chroma C. First, a colorimeter measures tristimulus values, X,Y,Z of the XYZ trichromatic system for light from a light source (step S10). Then, the calorimeter measures tristimulus values, X',Y',Z' for reflected light from a particular visual object (step S11). Finally, chroma C is obtained by calculating these values in accordance with the CIE Model (step S12).

Figure 17:
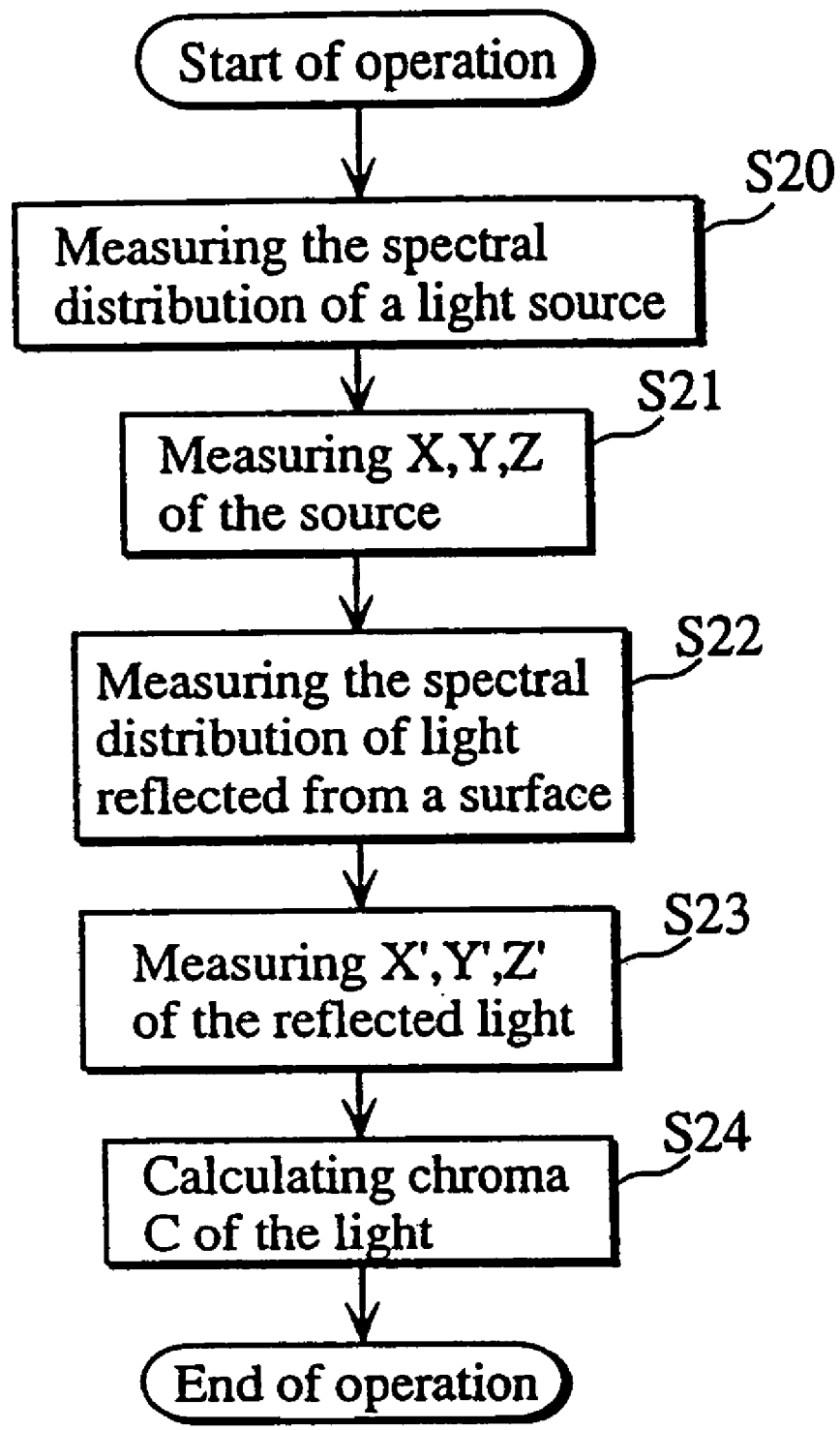
FIG. 17 is a flow chart showing the second procedure of calculating chroma according to a modification to the invention.

FIG. 17 shows a flow chart describing another processing contents to obtain chroma C. First, a luminance meter measures spectral distribution of light from a light source (step S20). Based on the spectral distribution, tristimulus values, X,Y,Z for radiation from a light source are determined (step S21). Then, the luminance meter measures spectral distribution of reflected light from a particular visual object (step S22), and determines tristimulus values, X',Y',Z' for the light based on the spectral distribution (step S23). Finally, these values are substituted into the CIE Model to obtain chroma C (step S24).

Figure 18:
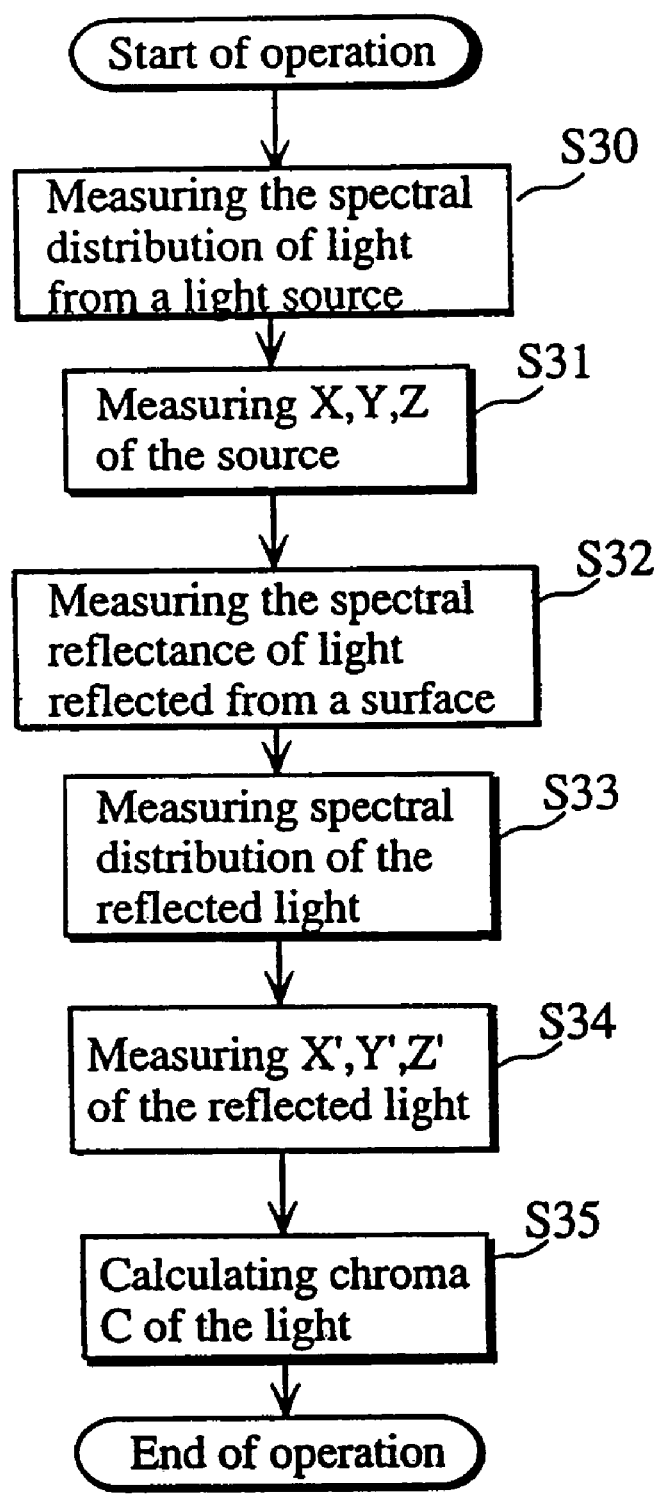
FIG. 18 is a flow chart showing the first procedure of calculating chroma according to a modification to the invention.

There's another way to obtain chroma C. FIG. 18 shows a flow chart describing processing contents to obtain chroma C. As is described in FIG. 17, in FIG. 18 a luminance meter measures spectral distribution of light from a light source (step S30), and determines tristimulus values, X,Y,Z for the light based on the spectral distribution. Then, a spectrophotometer measures spectral reflectance of the object (step S33). Based on the spectral distribution and the spectral reflectance, spectral distribution of light reflected from the object is calculated (step S33). When tristimulus values X',Y',Z' are determined based on the spectral distribution (step S34), these values are calculated in accordance with the CIE Model to obtain chroma C (step S35).

As a colorimeter, recommended are BM-5A (TOPCON Corporation) and luminance meters, CS-1000 (Minolta Co., Ltd.) and SR-3 (TOPCON Corporation). As a spectrophotometer, CM-3530 (Minolta Co., Ltd.) is recommended.

(2) Whiteness, given by using the methods mentioned above, is whiteness measured on the interval scale. In such a case, comparative whiteness between 70 and 80 is equivalent to comparative whiteness between 80 and 90.

If a label is displayed on a lamp to show whiteness on the ratio scale, together with whiteness on the interval scale, it helps consumers compare whiteness of one lamp with whiteness of another. A ratio scale, comparative whiteness Wc, would best suites for the purpose, which is the following.

To obtain comparative whiteness Wc between two light sources, the first step is to obtain chroma C1 for light from a first light source and chroma C2 for light from a second light source, according to the CIE Model. Then, those chroma values are substituted into the following equation (B).

$$Wc = (C1 - C2)/C1 \tag{B}$$

In this way, an objective ratio scale, independent of a subjective evaluation method, can be obtained.

Although the present invention has been fully described by way of examples with reference to the accompanying drawings, it is to be noted that various changes and modifications will be apparent to those skilled in the art.

Therefore, unless such changes and modifications depart from the scope of the present invention, they should be construed as being included therein.

What is claimed is:
1. A light source comprising:
a fluorescent lamp that contains a phosphor layer emitting light whose peak emissions are in four wavelength ranges of 440 nm to 470 nm, 505 nm to 530 nm, 540 nm to 570 nm, and 600 nm to 620 nm; and
wherein at least 70 wt % of the phosphor layer is a combination of:

a phosphor containing bivalent europium as an emission center and having a peak emission in a wavelength range of 440 nm to 470 nm;
a phosphor containing bivalent manganese as an emission center and having a peak emission in a wavelength range of 505 nm to 530 nm;
a phosphor containing trivalent terbium as an emission center and having a peak emission in a wavelength range of 540 nm to 570 nm; and
a phosphor containing trivalent europium as an emission center and having a peak emission in a wavelength range of 600 nm to 620 nm, and
the light source emitting light whose whiteness W is no smaller than 65 obtained when the light emitted by the light source is reflected from a blank surface of a newspaper, the whiteness W being calculated using an equation (7), $$W = -3.3C + 100 \tag{7}$$

wherein C is chroma of the light emitted by the light source, calculated with a method defined by the CIE 1997 Interim Color Appearance Model (Simple Version);
emitting light whose chromaticity is, on the CIE 1931 chromaticity diagram, in a range expressed by two equations (8) and (9); and
emitting light whose visual clarity index is no smaller than 110:

$$y \geq -2.63x^2 + 2.63x - 0.263 \tag{8}$$

$$y \geq -3.09x + 1.22 \tag{9},$$

wherein the light emitted by the light source has a correlated color temperature T[K] satisfying an inequality (4) related to a ratio of a radiant energy Qv in a wavelength range of 380 nm to 780 nm to radiant energy Qg in a wavelength range of 505 nm to 530 nm, $$Qg/Qv \geq -0.11 \times 10^4/T + 0.30 \tag{4}.$$

2. The light source of claim 1,
wherein the phosphor containing the bivalent europium as an emission center and having a peak emission in a wavelength range of 440 nm to 470 nm is composed of at least one of:
$BaMgAl_{10}O_{17}:Eu^{2+}$;
$BaMgAl_{10}O_{17}:Eu^{2+}, Mn^{2+}$; and
$(Ba, Ca, Sr, Mg)_{10}(PO_4)_6Cl_2:Eu^{2+}$, host crystals which are made up of Ba, Ca, Sr and Mg;
wherein compounds on the left side denote host crystals, and ions on the right side are emission centers contained in the phosphors.

3. The light source of claim 1,
wherein the phosphor containing the bivalent manganese as an emission center and having a peak emission at a wavelength range of 505 nm to 530 nm is composed of at least one of:
$BaMgAl_{10}O_{17}:Eu^{2+}, Mn^{2+}$;
$CeMgAl_{11}O_{19}:Mn^{2+}$;
$Ce(Mg, Zn)Al_{11}O_{19}:Mn^{2+}$;
$Zn_2SiO_4:Mn^{2+}$; and
$CeMgAl_{11}O_{19}:Tb^{2+}, Mn^{2+}$
wherein compounds on the left side denote host crystals, and ions on to right side are emission centers contained in the phosphors.

4. The light source of claim 1,
wherein the phosphor containing the trivalent terbium as an emission center and having an emission peak at a wavelength range of 540 nm to 570 nm is composed of at least one of:
$LaPO_4:Ce^{3+}, Tb^{3+}$; and
$CeMgAl_{11}O_{19}:Tb^{3+}$
wherein compounds on the left side denote host crystals and ions on the right side are emission centers contained in the phosphors.

5. The light source of claim 1,
wherein the phosphor containing the trivalent europium as an emission center and having an emission peak at a wavelength range of 600 nm to 620 nm is composed of at least one of:
$Y_2O_3:Eu^{2+}$; and
$Gd_2O_3:Eu^{3+}$
wherein compounds on the left side denote host crystals, and ions on the right side are emission centers contained in the phosphors.

6. A light source comprising:
a fluorescent lamp that contains a phosphor layer emitting light whose peak emissions are in four wavelength ranges of 440 nm to 470 nm, 505 nm to 530 nm, 540 nm to 570 nm, and 600 nm to 620 nm; and
wherein at least 70 wt % of the phosphor layer is a combination of:
a phosphor containing both bivalent europium and bivalent manganese as emission centers and having emission peaks both in wavelength ranges of 440 nm to 470 nm and 505 nm to 530 nm;
a phosphor containing trivalent terbium as an emission center and having an emission peak in a wavelength range of 540 nm to 570 nm; and
a phosphor containing trivalent europium as an emission center and having an emission peak in a wavelength range of 600 nm to 620 nm; and
the light source emitting light whose whiteness W is no smaller than 65 obtained when the light emitted by the light source is reflected from a blank surface of a newspaper, the whiteness W being calculated using an equation (7), $$W=-3.3C+100 \qquad (7)$$

wherein C is chroma of the light emitted by the light source calculated with a method defined by the CIE 1997 Interim Color Appearance Model (Simple Version);
emitting light whose chromaticity is, on the CIE 1931 chromaticity diagram, in a range expressed by two equations (8) and (9); and
emitting light whose visual clarity index is no smaller than 110:

$$y \geq -2.63x^2+2.63x-0.263 \qquad (8)$$

$$y \geq -3.09x+1.22 \qquad (9)$$

wherein the light emitted by the light source has a correlated color temperature T[K] satisfying an inequality (4) related to a ratio of a radiant energy Qv in a wavelength range of 380 nm to 780 nm to a radiant energy Qg in a wavelength range of 505 nm to 530 nm, $$Qg/Qv \geq -0.11 \times 10^4/T+0.30 \qquad (4).$$

7. The light Source of claim 6,
wherein the phosphor containing the bivalent europium and bivalent manganese as emission centers and having emission peaks both in wavelength ranges of 440 nm to 470 nm and at 505 nm to 530 nm is $BaMgAl_{10}O_{17}:Eu^{2+}, Mn^{2+}$
wherein a compound on the left side denotes a host crystal, and ions on the right side are emission centers contained in the phosphor.

8. The light source of claim 6,
wherein the phosphor containing the trivalent terbium as an emission center and having an emission peak at a wavelength range of 540 nm to 570 nm is composed of at least one of:
$LaPO_4:Ce^{3+}, Tb^{3+}$; and
$CeMgAl_{11}O_{19}:Tb^{3+}$
wherein compounds on the left side denote host crystals, and ions on the right side are emission centers contained in the phosphors.

9. The light source of claim 6,
wherein the phosphor containing the trivalent europium as an emission center and having an emission peak at a wavelength range of 600 nm to 620 nm is composed of at least one of:
$Y_2O_3:Eu^{3+}$; and
$Gd_2O_3:Eu^{3+}$
wherein compounds on the left side denote host crystals, and ions on the right side are emission centers contained in the phosphors.

10. A light source comprising:
a fluorescent lamp that contains a phosphor layer emitting light whose peak emissions are in four wavelength ranges of 440 nm to 470 nm, 505 nm to 530 nm, 540 nm to 570 nm, and 600 nm to 620 nm; and
wherein at least 70 wt % of the phosphor layer is a combination of;
a phosphor containing bivalent europium as an emission center and having an emission peak in a wavelength range of 440 nm to 471 nm;
a phosphor containing both trivalent terbium and bivalent manganese as emission centers and having emission peaks both in wavelength ranges of 505 nm to 530 nm and 540 nm to 570 nm; and
a phosphor containing trivalent europium as an emission center and having an emission peak in a wavelength range 600 nm to 620 nm, and
the light source emitting light whose whiteness W is no smaller than 65 obtained when the light emitted by the light source is reflected from a blank surface of a newspaper, the whiteness W being calculated using equation (7)

$$W=-3.3C+100 \qquad (7)$$

wherein C is chroma of the light emitted by the light source, calculated with a method defined by the CIE 1997 Interim Color Appearance Model (Simple Version);
emitting light whose chromaticity is, on the CIE 1931 chromaticity diagram, in a range expressed by two equations (8) and (9); and
emitting light whose visual clarity index is no smaller than 110:

$$y \geq -2.63x^2+2.63x-0.263 \qquad (8)$$

$$y \geq -3.09x+1.22 \qquad (9),$$

wherein the light emitted by the light source has a correlated color temperature T[K] satisfying an inequality (4) related to a ratio of a radiant energy Qv in a wavelength range of 380 nm to 780 nm to a radiant energy Qg in a wavelength range of 505 nm to 530 nm, $$Qg/Qv \geq -0.11 \times 10^4/T + 0.30 \qquad (4).$$

11. The light source of claim 10,
wherein the phosphor containing the bivalent europium as an emission center and having a peak emission in a wavelength range of 440 nm to 470 nm is composed of at least one of:
$BaMgAl_{10}O_{17}:Eu^{2+}$;
$BaMgAl_{10}O_{17}:Eu^{2+}, Mn^{2+}$; and
$(Ba, Ca, Sr, Mg)_{10}(PO_4)_6Cl_2:Eu^{2+}$, host crystals which are made up of Ba, Ca, Sr and Mg;
wherein compounds on the left side denote host crystals, and ions on the right side are emission centers contained in the phosphors.

12. The light source of claim 10,
wherein the phosphor containing the trivalent terbium and the bivalent manganese as emission centers and having peak emissions both at a wavelength range of 505 nm to 530 nm and at 540 nm to 570 nm is
$CeMgAl_{11}O_{19}:Tb^{3+}, Mn^{2+}$
wherein a compound on the left side denotes a host crystal, and ions on the right side are mission centers contained in the phosphor.

13. The light source of claim 10,
wherein the phosphor containing the trivalent europium as an emission center and having an emission peak at a wavelength range of 600 nm to 620 nm is composed of at least one of:
$Y_2O_3:Eu^{3+}$; and
$Gd_2O_3:Eu^{3+}$
wherein compounds on the left side denote host crystals, and ions on the right side are emission centers contained in the phosphors.

14. A light source comprising:
a fluorescent lamp containing a phosphor layer, the light source emitting light whose peak emissions are in four wavelength ranges of 440 nm to 470 nm, 505 nm to 530 nm, 540 nm to 570 nm, and 600 nm to 620 nm; and
wherein at least 70 wt % of the phosphor layer is a combination of;
a phosphor containing bivalent Europium as an emission center and having a peak emission in a wavelength range of 440 nm to 470 nm;
a phosphor containing bivalent manganese as an emission center and having a peak emission in a wavelength range of 505 nm to 530 nm;
a phosphor containing trivalent terbium as an emission center and having a peak emission in a wavelength range of 540 nm to 570 nm; and
a phosphor containing trivalent europium as an emission center and having a peak emission in a wavelength range of 600 nm to 620 nm, and
the light source emitting light whose whiteness W is no smaller than 65 obtained when the light emitted by the light source is reflected from a blank surface of a newspaper, the whiteness W being calculated using an equation (11), $$W = -3.3C + 100 \qquad (11)$$

wherein C is chroma of the light emitted by the light source, calculated with a method defined by the CIE 1997 Interim Color Appearance Model (Simple Version);
emitting light whose chromaticity is, on the CIE 1931 chromaticity diagram, in a range expressed by two equations (12) and (13); and
emitting light whose visual clarity index is no smaller than 115:

$$y \geq -2.63x^2 + 2.63x - 0.263 \qquad (12)$$

$$y \geq -3.09x + 1.22 \qquad (13),$$

wherein the light emitted by the light source has a correlated color temperature T[K] satisfying an inequality (14) related to a ratio of a radiant energy Qv in a wavelength range of 380 nm to 780 nm to a radiant energy Qg in a wavelength range of 505 nm to 530 nm, $$Qg/Qv \geq 0.11 \times 10^4/T + 0.30 \qquad (14).$$

15. The light source of claim 14,
wherein the phosphor containing the bivalent europium as an emission center and having a peak emission at a wavelength range of 440 nm to 470 nm is composed of at least one of:
$BaMgAl_{10}O_{17}:Eu^{2+}$;
$BaMgAl_{10}O_{17}:Eu^{2+}, Mn^{2+}$; and
$(Ba, Ca, Sr, Mg)_{10}(PO_4)_6Cl_2:Eu^{2+}$, host crystals which are made up of Ba, Ca, Sr and Mg;
wherein compounds on the left side denote host crystals, and ions on the right side are emission centers contained in the phosphors.

16. The light source of claim 14,
wherein the phosphor containing the bivalent manganese as an emission center and having a peak emission at a wavelength range of 505 nm to 530 nm is composed of at least one of:
$BaMgAl_{10}O_{17}:Eu^{2+}, Mn^{2+}$;
$CeMgAl_{11}O_{19}:Mn^{2+}$;
$Ce(Mg, Zn)Al_{11}O_{19}:Mn^{2+}$;
$Zn_2SiO_4:Mn^{2+}$; and
$CeMgAl_{11}O_{19}:Tb^{3+}, Mn^{2+}$
wherein compounds on the left side denote host crystals, and ions on the right side are emission centers contained in the phosphors.

17. The light source of claim 14,
wherein the phosphor containing to trivalent terbium is an emission center and having an emission peak at a wavelength range of 540 nm to 570 nm is composed of at least one of:
$LaPO_4:Ce^{3+}, Tb^{3+}$; and
$CeMgAl_{11}O_{19}:Tb^{3+}$
wherein compounds on the left side denote host crystals, and ions on the right side are emission centers contained in the phosphors.

18. The light source of claim 14,
wherein the phosphor containing the trivalent europium as an emission center and having an emission peak at a wavelength range of 600 nm to 620 nm is composed of at least one of:
$Y_2O_3:Eu^{3+}$; and
$Gd_2O_3:Eu^{3+}$
wherein compounds on the left side denote host crystals, and ions on the right side are emission centers contained in the phosphors.

19. A light source comprising:
a fluorescent lamp containing a phosphor layer, the light source emitting light whose peak emissions are in four wavelength ranges of 440 nm to 470 nm, 505 nm to 530 nm, 540 nm to 570 nm, and 600 nm to 620 nm; and wherein at least 70 wt % of the phosphor layer is a combination of;
a phosphor containing both bivalent europium and bivalent manganese as emission centers and having emission peaks both in wavelength ranges of 440 nm to 470 nm and 505 nm to 530 nm;
a phosphor containing trivalent terbium as an emission center and having an emission peak in a wavelength range of 540 nm to 574 nm; and
a phosphor containing trivalent europium an emission center and having an emission peak in a wavelength range of 600 nm to 620 nm, and
the light source emitting light whose whiteness W is no smaller than 65 when the light is reflected from a blank surface of a newspaper, the whiteness W being calculated using an equation (11), $$W = -3.3C + 100 \quad (11)$$

wherein C is chroma of the light emitted by the light source, calculated with a method defined by the CIE 1997 Interim Color Appearance Model (Simple Version);
emitting light whose chromaticity is, on the CIE 1931 chromaticity diagram, in a range expressed by two equations (12) and (13); and
emitting light whose visual clarity index is no smaller than 115:

$$y \geq -2.63x^2 + 2.63x - 0.263 \quad (12)$$

$$y \geq -3.09x + 1.22 \quad (13),$$

wherein the light emitted by the light source has a correlated color temperature T[K] satisfying an inequality (14) related to a ratio of a radiant energy Qv in a wavelength range of 380 nm to 780 nm to a radiant energy Qg in a wavelength range of 505 nm to 530 nm, $$Qg/Qv \geq -0.11 \times 10^4/T + 0.30 \quad (14).$$

20. The light source of claim 19, wherein the phosphor containing the bivalent europium and bivalent manganese as emission centers and having emission peaks both at a wavelength rage of 440 nm to 470 nm and at 505 nm to 530 nm is
$BaMgAl_{10}O_{17}:Eu^{2+}, Mn^{2+}$
wherein a compound on the left side denotes a host crystal, and ions on the right side are emission centers contained in the phosphor.

21. The light source of claim 19, wherein the phosphor containing the trivalent terbium as an emission center and having an emission peak at a wavelength range of 540 nm to 570 nm is composed of at least one of:
$LaPO_4:Ce^{3+}, Tb^{3+}$; and
$CeMgAl_{11}O_{19}:Tb^{3+}$
wherein compounds on the left side denote host crystals, and ions on the right side are emission centers contained in the phosphors.

22. The light source of claim 19, wherein the phosphor containing the trivalent europium as an emission center and having an emission peak at a wavelength range of 600 nm to 620 nm is composed of at least one of:
$Y_2O_3:Eu^{3+}$; and
$Gd_2O_3:Eu^{3+}$
wherein compounds on the left side denote host crystals, and ions on the right side are emission centers contained in the phosphors.

23. A light source comprising:
a fluorescent lamp containing a phosphor layer, the light source emitting light whose peak emissions are in four wavelength ranges of 440 nm to 470 nm, 505 nm to 530 nm, 540 nm to 570 nm, and 600 nm to 620 nm; and
wherein at least 70 wt % of the phosphor layer is a combination of:
a phosphor containing bivalent europium as an emission center and having an emission peak in a wavelength range of 440 nm to 470 nm;
a phosphor containing both trivalent terbium and bivalent manganese as emission centers and having emission peaks both in wavelength ranges of 505 nm to 530 nm and 540 nm to 570 nm; and
a phosphor containing trivalent europium as an emission center and having an emission peak in a wavelength range of 600 nm to 620 nm, and
the light source emitting light whose whiteness W is no smaller than 65 obtained when the light emitted by the light source is reflected from a blank surface of a newspaper, the whiteness W being calculated using an equation (11), $$W = -3.3C + 100 \quad (11)$$

wherein C is chroma of the light emitted by the light source, calculated with a method defined by the CIE 1997 Interim Color Appearance Model(Simple Version);
emitting light whose chromaticity is, on the CIE 1931 chromaticity diagram, in a range expressed by two equations (12) and (13); and
emitting light whose visual clarity index is no smaller than 115:

$$y \geq -2.63x^2 + 2.63x - 0.263 \quad (12)$$

$$y \geq -3.09x + 1.22 \quad (13),$$

wherein the light emitted by the light source has a correlated color temperature T[K] satisfying an inequality (14) related to a ratio of a radiant energy Qv in a wavelength range of 380 nm to 780 nm to a radiant energy Qg in a wavelength range of 505 nm to 530 nm, $$Qg/Qv \geq -0.11 \times 10^4/T + 0.30 \quad (14).$$

24. The light source of claim 23, wherein the phosphor containing the bivalent europium as an emission center and having a peak emission in a wavelength range of 440 nm to 470 nm is composed of at least one of:
$BaMgAl_{10}O_{17}:Eu^{2+}$;
$BaMgAl_{10}O_{17}:Eu^{2+}, Mn^{2+}$; and
$(Ba, Ca, Sr, Mg)10(PO_4)_5 Cl_2:Eu^{2+}$, host crystals which are made up of Ba, Ca, Sr and Mg;
wherein compounds on the left side denote host crystals, and ions on the right side are emission centers contained in the phosphors.

25. The light source of claim 23, wherein the phosphor containing the trivalent terbium and the bivalent manganese as emission centers and having peak emissions both at a wavelength range of 505 nm to 530 nm and at 540 nm to 579 nm is
$CeMgAl_{11}O_{19}:Tb^{3+}, Mn^{2+}$ wherein a compound on the left side denotes a host crystal, and ions on the right side are emission centers contained in the phosphor.

26. The light source of claim 23,
wherein the phosphor containing the trivalent europium as an emission center and having an emission peak at a wavelength range of 600 nm to 620 nm is composed of at least one of:

$Y_2O_3:Eu^{3+}$; and $Gd_2O_3:Eu^{3+}$ wherein compounds on the left side denote host crystals, and ions on the right side are emission centers contained in the phosphors.

* * * * *